US012599600B2

(12) United States Patent

Largent-Milnes et al.

(10) Patent No.: US 12,599,600 B2

(45) Date of Patent: Apr. 14, 2026

(54) COMPOSITIONS AND METHODS FOR PREVENTING AND TREATING HEADACHE THROUGH ENHANCING 2-ARACHYDONYL GLYEROL ACTIVITY

(71) Applicants: Arizona Board of Regents on Behalf of the University of Arizona, Tucson, AZ (US); University of Washington, Seattle, WA (US)

(72) Inventors: Tally M. Largent-Milnes, Tucson, AZ (US); Erika Liktor-Busa, Tucson, AZ (US); Todd W. Vanderah, Tucson, AZ (US); Nephi Stella, Seattle, WA (US)

(73) Assignees: Arizona Board of Regents on Behalf of the University of Arizona, Tucson, AZ (US); University of Washington, Seattle, WA (US)

( * ) Notice: Subject to any disclaimer, the term of this patent is extended or adjusted under 35 U.S.C. 154(b) by 191 days.

(21) Appl. No.: 17/331,025

(22) Filed: May 26, 2021

(65) Prior Publication Data

US 2021/0369704 A1 Dec. 2, 2021

Related U.S. Application Data

(60) Provisional application No. 63/032,183, filed on May 29, 2020.

(51) Int. Cl.

| | |
|---|---|
| ***A61K 31/496*** | (2006.01) |
| ***A61K 31/454*** | (2006.01) |
| ***A61K 45/06*** | (2006.01) |
| ***A61P 25/06*** | (2006.01) |

(52) U.S. Cl.

CPC .......... *A61K 31/496* (2013.01); *A61K 31/454* (2013.01); *A61K 45/06* (2013.01); *A61P 25/06* (2018.01)

(58) Field of Classification Search

CPC .... A61K 31/454; A61K 31/496; A61K 45/06; A61K 2300/00; A61P 25/06

See application file for complete search history.

(56) References Cited

U.S. PATENT DOCUMENTS

| | | | | |
|---|---|---|---|---|
| 2005/0284792 A1* | 12/2005 | Gopinathan | ........... | B65D 23/12 206/528 |
| 2018/0099951 A1* | 4/2018 | Blankman | ............... | A61P 29/00 |
| 2019/0015297 A1 | 1/2019 | Harada | | |

OTHER PUBLICATIONS

Alhouayek et al., Controlling 2-arachidonoylglycerol metabolism as an anti-inflammatory strategy, Drug Discovery today, vol. 19, No. 3, 295-304, Mar. 2014 (Year: 2014).*

(Continued)

*Primary Examiner* — Kortney L. Klinkel

*Assistant Examiner* — Padmaja S Rao

(74) *Attorney, Agent, or Firm* — Casimir Jones, S.C.; Robert A. Goetz

(57) ABSTRACT

This invention relates generally to compositions and methods for preventing, reducing the occurrence of or treating a headache in a subject in need thereof. In particular, the present invention relates to methods for enhancing 2-arachydonyl glycerol (2AG) tone and reducing prostaglandin activity in a subject for purposes of preventing, reducing the occurrence of or treating a headache (e.g., a migraine headache) in a subject.

5 Claims, 8 Drawing Sheets

Specification includes a Sequence Listing.

(56) References Cited

OTHER PUBLICATIONS

Hsu et al., Discovery and Optimization of Piperidyl-1,2,3-Triazole Ureas as Potent, Selective, and in Vivo-Active Inhibitors of α/β-Hydrolase Domain Containing 6 (ABHD6), Journal of Medicinal Chemistry, vol. 56, 8270-8279, Oct. 23, 2013 (Year: 2013).*
Greco et al., Endocannabinoid System and Migraine Pain: An Update, Frontiers in Neuroscience, vol. 12, No. 172, 1-7, Mar. 19, 2018 (Year: 2018).*
Burch, R.C., et al., The prevalence and burden of migraine and severe headache in the United States: updated statistics from government health surveillance studies. Headache, 2015. 55(1): p. 21-34.
Global, regional, and national burden of migraine and tension-type headache, 1990-2016: a systematic analysis for the Global Burden of Disease Study 2016. Lancet Neurol, 2018. 17(11): p. 954-976.
Smitherman, T.A., et al., The prevalence, impact, and treatment of migraine and severe headache in the United States: a review of statistics from national surveillance studies. Headache, 2013. 53(3): p. 427-36.
Silberstein, S.D., Headache and female hormones: what you need to know. Curr Opin Neurol, 2001. 14(3): p. 323-33.
Eikermann-Haerter, K., et al., Genetic and hormonal factors modulate spreading depression and transient hemiparesis in mouse models of familial hemiplegic migraine type 1. J Clin Invest, 2009. 119(1): p. 99-109.
Fioravanti, B., et al., Evaluation of cutaneous allodynia following induction of.
Gault, L.M., et al., Changes in energy metabolites, cGMP and intracellular pH during cortical spreading depression. Brain Res, 1994. 641(1): p. 176-80.
Pusic, A.D., et al., Spreading depression transiently disrupts myelin via interferon-gamma signaling. Experimental neurology, 2015. 264: p. 43-54.
Cozzolino, O., et al., Understanding Spreading Depression from Headache to Sudden Unexpected Death. Frontiers in Neurology, 2018. 9(19).
Hartings, J.A., et al., The continuum of spreading depolarizations in acute cortical lesion development: Examining Leao's legacy. J Cereb Blood Flow Metab, 2017. 37(5): p. 1571-1594.
Lauritzen, M., et al., Clinical relevance of cortical spreading depression in neurological disorders: migraine, malignant stroke, subarachnoid and intracranial hemorrhage, and traumatic brain injury. J Cereb Blood Flow Metab, 2011. 31(1): p. 17-35.
Andrew, R.D., Y.T. Hsieh, and C.D. Brisson, Spreading depolarization triggered by elevated potassium is weak or absent in the rodent lower brain. J Cereb Blood Flow Metab, 2017. 37(5): p. 1735-1747.
Csiba, L., W. Paschen, and G. Mies, Regional changes in tissue pH and glucose content during cortical spreading depression in rat brain. Brain Res, 1985. 336(1): p. 167-70.
Kurauchi, Y., et al., Propranolol prevents cerebral blood flow changes and pain-related behaviors in migraine model mice. Biochem Biophys Res Commun, 2019. 508(2): p. 445-450.
Moskowitz, M.A., The neurobiology of vascular head pain. Ann Neurol, 1984. 16(2): p. 157-68.
Sun, X., et al., Simultaneous monitoring of intracellular pH changes and hemodynamic response during cortical spreading depression by fluorescence-corrected multimodal optical imaging. Neuroimage, 2011. 57(3): p. 873-84.
Harriott, A.M., et al., Spreading depression as a preclinical model of migraine. J Headache Pain, 2019. 20(1): p. 45.
Hansen, A.J. and T. Zeuthen, Extracellular ion concentrations during spreading depression and ischemia in the rat brain cortex. Acta Physiol Scand, 1981. 113(4): p. 437-45.
Jacobs, B. and G. Dussor, Neurovascular contributions to migraine: Moving beyond vasodilation. Neuroscience, 2016. 338: p. 130-144.
Busija, D.W., et al., Mechanisms involved in the cerebrovascular dilator effects of cortical spreading depression. Prog Neurobiol, 2008. 86(4): p. 379-95.
Blicher, J.U., et al., Perfusion and pH MRI in familial hemiplegic migraine with prolonged aura. Cephalalgia, 2015.
Cernuda-Morollon, E., et al., Interictal increase of CGRP levels in peripheral blood as a biomarker for chronic migraine. Neurology, 2013. 81(14): p. 1191-6.
Durham, P. and S. Papapetropoulos, Biomarkers associated with migraine and their potential role in migraine management. Headache, 2013. 53(8): p. 1262- 77.
Boes, T. and D. Levy, Influence of sex, estrous cycle, and estrogen on intracranial dural mast cells. Cephalalgia, 2012. 32(12): p. 924-31.
Edelmayer, R.M., M.H. Ossipov, and F. Porreca, An experimental model of headache-related pain. Methods Mol Biol, 2012. 851: p. 109-20.
Lundblad, C., et al., Experimental inflammation following dural application of complete Freund's adjuvant or inflammatory soup does not alter brain and trigeminal microvascular passage. J Headache Pain, 2015. 16(1): p. 91.
Yan, J., et al., pH-evoked dural afferent signaling is mediated by ASIC3 and is sensitized by mast cell mediators. Headache, 2013. 53(8): p. 1250-61.
Hadjikhani, N., et al., Mechanisms of migraine aura revealed by functional MRI in human visual cortex. Proc Natl Acad Sci U S A, 2001. 98(8): p. 4687-92.
Edelmayer, R.M., et al., Activation of TRPA1 on dural afferents: a potential mechanism of headache pain. Pain, 2012. 153(9): p. 1949-58.
Edelmayer, R.M., et al., Medullary pain facilitating neurons mediate allodynia in headache-related pain. Ann Neurol, 2009. 65(2): p. 184-93.
Marshall, A.C., et al., Evidence for an angiotensin-(1-7) neuropeptidase expressed in the brain medulla and CSF of sheep. J Neurochem, 2014. 130(2): p. 313-23.
Stucky, N.L., et al., Sex differences in behavior and expression of CGRP-related genes in a rodent model of chronic migraine. Headache, 2011. 51(5): p. 674-92.
Kandasamy, R., A.T. Lee, and M.M. Morgan, Depression of home cage wheel running: a reliable and clinically relevant method to assess migraine pain in rats. J Headache Pain, 2017. 18(1): p. 5.
Khanna, R., et al., Development and Characterization of an Injury-free Model of Functional Pain in Rats by Exposure to Red Light. J Pain, 2019.
Reggio, P.H., Endocannabinoid binding to the cannabinoid receptors: what is known and what remains unknown. Current medicinal chemistry, 2010. 17(14): p. 1468-1486.
Jia, Z., et al., Disrupted functional connectivity between the periaqueductal gray and other brain regions in a rat model of recurrent headache. Sci Rep, 2017. 7(1): p. 3960.
Chanda, D., D. Neumann, and J.F.C. Glatz, The endocannabinoid system: Overview of an emerging multi-faceted therapeutic target. Prostaglandins Leukot Essent Fatty Acids, 2019. 140: p. 51-56.
Nomura, D.K., et al., Endocannabinoid hydrolysis generates brain prostaglandins that promote neuroinflammation. Science, 2011. 334(6057): p. 809-13.
Yirmiya, R. and I. Goshen, Immune modulation of learning, memory, neural plasticity and neurogenesis. Brain Behav Immun, 2011. 25(2): p. 181-213.
Sundrum, T. and C.S. Walker, Pituitary adenylate cyclase-activating polypeptide receptors in the trigeminovascular system: implications for migraine. Br J Pharmacol, 2018. 175(21): p. 4109-4120.
Formicola, D., et al., Common variants in the regulative regions of GRIA1 and GRIA3 receptor genes are associated with migraine susceptibility. BMC Med Genet, 2010. 11: p. 103.
Hollenstein, K., et al., Insights into the structure of class B GPCRs. Trends Pharmacol Sci, 2014. 35(1): p. 12-22.
Stone, L.S. and D.C. Molliver, In search of analgesia: emerging roles of GPCRs in pain. Mol Interv, 2009. 9(5): p. 234-51.
Soethoudt, M., et al., Cannabinoid CB2 receptor ligand profiling reveals biased signalling and off-target activity. Nature Communications, 2017. 8(1): p. 13958.
Harlan, B.A., et al., Opposing actions of CRF-R1 and CB1 receptors on VTA-GABAergic plasticity following chronic exposure to ethanol. Neuropsychopharmacology, 2018. 43(10): p. 2064-2074.

(56) References Cited

OTHER PUBLICATIONS

Hoffman, A.F., A.C. Riegel, and C.R. Lupica, Functional localization of cannabinoid receptors and endogenous cannabinoid production in distinct neuron populations of the hippocampus. Eur J Neurosci, 2003. 18(3): p. 524-34.
Sanchez-Blazquez, P., M. Rodriguez-Munoz, and J. Garzon, The cannabinoid receptor 1 associates with NMDA receptors to produce glutamatergic hypofunction: implications in psychosis and schizophrenia. Front Pharmacol, 2014. 4: p. 169.
Murataeva, N., A. Straiker, and K. Mackie, Parsing the players: 2-arachidonoylglycerol synthesis and degradation in the CNS. British journal of pharmacology, 2014. 171(6): p. 1379-1391.
Gong, J.P., et al., Cannabinoid CB2 receptors: immunohistochemical localization in rat brain. Brain Res, 2006. 1071(1): p. 10-23.
Navarrete, F., et al., Role of CB2 cannabinoid receptors in the rewarding, reinforcing, and physical effects of nicotine. Neuropsychopharmacology, 2013. 38(12): p. 2515-24.
Ortega-Alvaro, A., et al., Role of cannabinoid CB2 receptor in the reinforcing actions of ethanol. Addict Biol, 2015. 20(1): p. 43-55.
Xi, Z.X., et al., Brain cannabinoid CB(2) receptors modulate cocaine's actions in mice. Nat Neurosci, 2011. 14(9): p. 1160-6.
Zhang, H.Y., et al., Cannabinoid CB2 receptors modulate midbrain dopamine neuronal activity and dopaminerelated behavior in mice. Proc Natl Acad Sci U S A, 2014. 111(46): p. E5007-15.
Zhang J., H.C., Vu H.K., Groblewski T., Ahmad S., and O.D. D., Induction of CB2 receptor expression in the ratspinal cord of neuropathic but not inflammatory chronicpain models. European Journal of Neuroscience, 2003. 17 p. 2750-2754.
Grenald, S.A., et al., Synergistic attenuation of chronic pain using mu opioid and cannabinoid receptor 2 agonists. Neuropharmacology, 2017. 116: p. 59-70.
Ignatowska-Jankowska, B.M., et al., The cannabinoid CB2 receptor is necessary for nicotine-conditioned place preference, but not other behavioral effects of nicotine in mice. Psychopharmacology (Berl), 2013. 229(4): p. 591-601.
Cohen, C., E. Kodas, and G. Griebel, CB1 receptor antagonists for the treatment of nicotine addiction. Pharmacol Biochem Behav, 2005. 81(2): p. 387-95.
Cossu, G., et al., Cannabinoid CB1 receptor knockout mice fail to self-administer morphine but not other drugs of abuse. Behav Brain Res, 2001. 118(1): p. 61-5.
Covey, D.P., J.M. Wenzel, and J.F. Cheer, Cannabinoid modulation of drug reward and the implications of marijuana legalization. Brain Res, 2014.
Le Foll, B. and S.R. Goldberg, Rimonabant, a CB1 antagonist, blocks nicotine-conditioned place preferences. Neuroreport, 2004. 15(13): p. 2139-43.
Burston, J.J. and S.G. Woodhams, Endocannabinoid system and pain: an introduction. Proc Nutr Soc, 2014. 73(1): p. 106-17.
Sailler, S., et al., Regulation of circulating endocannabinoids associated with cancer and metastases in mice and humans. Oncoscience, 2014. 1(4): p. 272-82.
Abidi, A.H., et al., Anti-inflammatory activity of cannabinoid receptor 2 ligands in primary hPDL fibroblasts. Arch Oral Biol, 2018. 87: p. 79-85.
Luk, T., et al., Identification of a potent and highly efficacious, yet slowly desensitizing CB1 cannabinoid receptor agonist. Br J Pharmacol, 2004. 142(3): p. 495-500.
Kind, L. and P. Kursula, Structural properties and role of the endocannabinoid lipases ABHD6 and ABHD12 in lipid signalling and disease. Amino Acids, 2019. 51(2): p. 151-174.
Dhopeshwarkar, A. and K. Mackie, Functional Selectivity of CB2 Cannabinoid Receptor Ligands at a Canonical and Noncanonical Pathway. J Pharmacol Exp Ther, 2016. 358(2): p. 342-51.
Cao, J.K., J. Kaplan, and N. Stella, ABHD6: Its Place in Endocannabinoid Signaling and Beyond. Trends Pharmacol Sci, 2019. 40(4): p. 267-277.
Marrs, W.R., et al., The serine hydrolase ABHD6 controls the accumulation and efficacy of 2-AG at cannabinoid receptors. Nat Neurosci, 2010. 13(8): p. 951-7.
Anderson, W.B., et al., Actions of the dual FAAH/MAGL inhibitor JZL 195 in a murine inflammatory pain model. Neuropharmacology, 2014. 81: p. 224-30.
Davis, M.P., Cannabinoids in pain management: CB1, CB2 and non-classic receptor ligands. Expert Opin Investig Drugs, 2014. 23(8): p. 1123-40.
Ibrahim, M.M., et al., CB2 cannabinoid receptor mediation of antinociception. Pain, 2006. 122(1-2): p. 36-42.
Lozano-Ondoua, A.N., et al., Disease modification of breast cancer-induced bone remodeling by cannabinoid 2 receptor agonists. J Bone Miner Res, 2013. 28(1): p. 92-107.
Lozano-Ondoua, A.N., et al., A cannabinoid 2 receptor agonist attenuates bone cancer-induced pain and bone loss. Life Sci, 2010. 86(17-18): p. 646-53.
Pascual, D., et al., A cannabinoid agonist, WIN 55,212-2, reduces neuropathic nociception induced by paclitaxel in rats. Pain, 2005. 118(1-2): p. 23-34.
Sarchielli, P., et al., Endocannabinoids in Chronic Migraine: CSF Findings Suggest a System Failure. Neuropsychopharmacology, 2007. 32(6): p. 1384-1390.
Greco, R., et al., Endocannabinoid System and Migraine Pain: An Update. Front Neurosci, 2018. 12. p. 172.
Russo, E.B. Clinical endocannabinoid deficiency (CECD): can this concept explain therapeutic benefits of cannabis in migraine, fibromyalgia, irritable bowel syndrome and other treatment-resistant conditions? Neuro Endocrinol Lett, 2008. 29(2): p. 192-200.
Global, regional, and national burden of neurological disorders, 1990-2016: a systematic analysis for the Global Burden of Disease Study 2016. Lancet Neurol, 2019. 18(5): p. 459-480.
Borsook, D., et al., Sex and the migraine brain. Neurobiol Dis, 2014. 68: p. 200-14.
Buse, D.C., et al., Sex differences in the prevalence, symptoms, and associated features of migraine, probable migraine and other severe headache: results of the American Migraine Prevalence and Prevention (AMPP) Study. Headache, 2013. 53(8): p. 1278-99.
Karli, N., et al., Impact of sex hormonal changes on tension-type headache and migraine: a cross-sectional population-based survey in 2,600 women. J Headache Pain, 2012. 13(7): p. 557-65.
Greco, R., et al., The endocannabinoid system and migraine. Exp Neurol 2010. 224(1): p. 85-91.
Cupini, L.M., et al., Biochemical changes in endocannabinoid system are expressed in platelets of female but not male migraineurs. Cephalalgia, 2006. 26(3): p. 277-81.
Baron, E.P., Medicinal Properties of Cannabinoids, Terpenes, and Flavonoids in Cannabis, and Benefits in Migraine, Headache, and Pain: An Update on Current Evidence and Cannabis Science. Headache, 2018. 58(7): p. 1139-1186.
Baron, E.P., et al., Patterns of medicinal cannabis use, strain analysis, and substitution effect among patients with migraine, headache, arthritis, and chronic pain in a medicinal cannabis cohort. J Headache Pain, 2018. 19(1): p. 37.
Forderreuther, S., [Cannabis in headache treatment]. MMW Fortschr Med, 2018. 160(Suppl 1): p. 70-71.
Lochte, B.C., et al., The Use of Cannabis for Headache Disorders. Cannabis Cannabinoid Res, 2017. 2(1): p. 61-71.
Banerjee, S. and S. McCormack, CADTH Rapid Response Reports, in Medical Cannabis for the Treatment of Chronic Pain: A Review of Clinical Effectiveness and Guidelines. 2019, Canadian Agency for Drugs and Technologies in Health. Copyright (c) 2019 Canadian Agency for Drugs and Technologies in Health.: Ottawa (ON).
Cuttler, C., et al., Short- and Long-Term Effects of Cannabis on Headache and Migraine. J Pain, 2019.
Adorjan, K., et al., Epileptic Spikes in EEG and Migraine Attacks in the Course of Cannabis Withdrawal: A Case Report. Clin EEG Neurosci, 2020. 51(1): p. 45-50.
Kandasamy, R., et al., Anti-migraine effect of (9)-tetrahydrocannabinol in the female rat. Eur J Pharmacol, 2018. 818: p. 271-277.
Kandasamy, R., et al., Medication overuse headache following repeated morphine, but not [INCREMENT]9-tetrahydrocannabinol administration in the female rat. Behav Pharmacol, 2018. 29(5): p. 469-472.

(56) References Cited

OTHER PUBLICATIONS

Kopruszinski, C.M., et al., Cannabinoids induce latent sensitization in a preclinical model of medication overuse headache. Cephalalgia, 2019: p. 333102419865252.
Leimuranta, P., et al., Emerging role of (endo)cannabinoids in migraine. Front Pharmacol 2018. 9: 420.
Nozaki, C., et al., Inhibition of FAAH reduces nitroglycerine-induced migraine- like pain and trigeminal neuronal hyperactivity in mice. Eur Neuropsychophramacol, 2015. 25(8): p. 1388-96.
Greco, R., et al., *Effects of peripheral FAAH blockade on NTG-induced hyperalgesia—evaluation of URB937 in an animal model of migraine*. Cephalgia, 2015. 35(12): p. 1065-76.
Rimplejeet, K., et al., What failed BIA 10-2474 Phase I clinical trial? Global speculations and recommendations for future Phase I trials. J Pharmacol Pharmacother, 2016. 7(3): p. 120-6.
Greco, R., et al., Inhibition of monoacylglycerol lipase: Another signalling pathway for potential therapeutic targets in migraine? Cephalalgia, 2018. 38(6): p. 1138-1147.
Greco, R., et al., FAAH inhibition as a preventive treatment for migraine: A pre-clinical study. Neurobiol Dis, 2019. 134: p. 104624.
Tuo, W., et al., Therapeutic potential of fatty acid amide hydrolase, monoacylglycerol lipase, and Nacylethanolamine acid amidase inhibitors. J Med Chem, 2017. 60(1): p. 4-46.
Adamson Barnes, N.S., et al., Actions of the dual FAAH/MAGL inhibitor JZL 195 in a murine neuropathic pain model. Br J Pharmacol, 2016. 173(1): p. 77-87.
Chang, J.W., et al., Highly selective inhibitors of monoacylglycerol lipase bearing a reactive group that is bioisosteric with endocannabinoid substrates. Chem Biol, 2012. 19(5): p. 579-88.
Kinsey, S.G., et al., Fatty acid amide hydrolase and monoacylglycerol lipase inhibitors produce anti-allodynic effects in mice through distinct cannabinoid receptor mechanisms. J Pain, 2010. 11(12): p. 1420-8.
Sakin, Y.S., et al., The effect of Faah, Magl, and Dual FAAH/MAGL inhibition on inflammatory and colorectal distension-induced visceral pain models in Rodents. Neurogastroenterol Motil, 2015. 27(7): p. 936-44.
Zubrzycki, M., et al., Effects of centrally administered endocannabinoids and opioids on orofacial pain perception in rats. Br J Pharmacol, 2017. 174(21): p. 3780-3789.
Lau, B.K., et al., Endocannabinoid modulation by FAAH and monoacylglycerol lipase within the analgesic circuitry of the periaqueductal grey. Br J Pharmacol, 2014. 171(23): p. 5225-36.
Owens, R.A., et al., Discriminative Stimulus Properties of the Endocannabinoid Catabolic Enzyme Inhibitor SA-57 in Mice. J Pharmacol Exp Ther, 2016. 358(2): p. 306-14.
Seillier, A., D. Dominguez Aguilar, and A. Giuffrida, The dual FAAH/MAGL inhibitor JZL195 has enhanced effects on endocannabinoid transmission and motor behavior in rats as compared to those of the MAGL inhibitor JZL184. Pharmacol Biochem Behav, 2014. 124: p. 153-9.
Bera, S.C., et al., A comparative study of psychiatric comorbidity, quality of life and disability in patients with migraine and tension type headache. Neurol India, 2014. 62(5): p. 516-20.
Dreier, Jens P. and C. Reiffurth, The Stroke-Migraine Depolarization Continuum. Neuron, 2015. 86(4): p. 902-922.
Dai, Y.J., et al., Potential Beneficial Effects of Probiotics on Human Migraine Headache: A Literature Review. Pain Physician, 2017. 20(2): p. E251-e255.
Evans, R.W., et al., The FDA alert on serotonin syndrome with use of triptans combined with selective serotonin reuptake inhibitors or selective serotonin-norepinephrine reuptake inhibitors: American Headache Society position paper. Headache, 2010. 50(6): p. 1089-99.
Louter, M.A., et al., Cutaneous allodynia as a predictor of migraine chronification. Brain, 2013. 136(11): p. 3489-3496.
Smith, S.C. and M.S. Wagner, Clinical endocannabinoid deficiency (CECD) revisited: can this concept explain the therapeutic benefits of cannabis in migraine, fibromyalgia, irritable bowel syndrome and other treatment-resistant conditions? Neuro Endocrinol Lett, 2014. 35(3): p. 198-201.
Guindon, J., et al., The endocannabinoid system and pain. CNS Neurol Disord Drug Targets, 2009. 8(6): 403-21.
Huang, W.J., et al., Endocannabinoid system: Role in depression, reward and pain control. Mol Med Rep, 2016. 14(4): 2899-903.
Kendall, D.A, et al., Cannabinoid Receptors in the Central Nervous System: Their Signaling and Roles in Disease. Front Cell Neurosci, 2017. 10: 294.
Cottier, K.E., et al., Loss of Blood-Brain Barrier Integrity in a KCl-Induced Model of Episodic Headache Enhances CNS Drug Delivery. eNeuro, 2018. 5(4).
Menyhart, A., et al., Large-conductance Ca(2+)-activated potassium channels are potently involved in the inverse neurovascular response to spreading depolarization. Neurobiol Dis, 2018. 119: p. 41-52.
Wang, Y., et al., Induction of calcitonin gene-related peptide expression in rats by cortical spreading depression. Cephalalgia, 2019. 39(3): p. 333-341.
Liktor-Busa, E., et al., Functional NHE1 expression is critical to blood brain barrier integrity and sumatriptan blood to brain uptake. bioRxiv, 2019: p. 2019.12.20.884247.
Mathew, N.T., Pathophysiology of chronic migraine and mode of action of preventive medications. Headache, 2011. 51 Suppl 2: p. 84-92.
Schwedt, T.J., et al., Allodynia and descending pain modulation in migraine: a resting state functional connectivity analysis. Pain Med, 2014. 15(1): p. 154-65.
Tietjen, G.E., et al., Allodynia in migraine: association with comorbid pain conditions. Headache, 2009. 49(9): p. 1333-44.
Charles, A. and K. Brennan, Cortical spreading depression-new insights and persistent questions. Cephalalgia, 2009. 29(10): p. 1115-24.
Eising, E., et al., Cortical Spreading Depression Causes Unique Dysregulation of Inflammatory Pathways in a Transgenic Mouse Model of Migraine. Mol Neurobiol, 2017. 54(4): p. 2986-2996.
Ayata, C., Pearls and pitfalls in experimental models of spreading depression. Cephalalgia, 2013. 33(8): p. 604-13.
Sandweiss, A.J, et al,. Genetic and pharmacological antagonism of NK1 receptor prevents opiate abuse potential. Mol Psychiatry, 2017. 23(8): p. 1745-55.
Ibrahim, M.M., et al., Long-lasting antinociceptive effects of green light in acute and chronic pain in rats. Pain, 2017. 158(2): p. 347-60.
Hegarty, D.M., et al., Capsaicin-responsive corneal afferents do not contain TRPV1 at their central terminals in trigeminal nucleus caudalis in rats. J Chem Neuroanat, 2014. 61-62: p. 1-12.
Fried, N.T., et al., Region-specific disruption of the blood-brain barrier following repeated inflammatory dural stimulation in a rat model of chronic trigeminal allodynia. Cephalalgia, 2018. 38(4): p. 674-689.
Avona, A., et al., Dural Calcitonin Gene-Related Peptide Produces Female-Specific Responses in Rodent Migraine Models. J Neurosci, 2019. 39(22): p. 4323-4331.
Tassorelli, C., et al., Nitroglycerin induces hyperalgesia in rats—a time-course study. Eur J Pharmacol, 2003. 464(2-3): p. 159-62.
Pardutz, A., et al., Nitroglycerin-induced nNOS increase in rat trigeminal nucleus caudalis is inhibited by systemic administration of lysine acetylsalicylate but not of sumatriptan. Cephalalgia, 2004. 24(6): p. 439-45.
De Felice, M., et al., Capturing the aversive state of cephalic pain preclinically. Ann Neurol, 2013. 74(2): p. 257-65.
Nation, K.M., et al., Sustained exposure to acute migraine medications combined with repeated noxious stimulation dysregulates descending pain modulatory circuits: Relevance to medication overuse headache. Cephalalgia, 2019. 39(5): p. 617-625.
Gibbs, R.A., et al., Genome sequence of the Brown Norway rat yields insights into mammalian evolution. Nature, 2004. 428(6982): p. 493-521.
Clayton, J.A., et al., Policy: NIH to balance sex in cell and animal studies. Nature, 2014. 509(7500): p. 282-3.
Andrews, N.A., et al., Ensuring transparency and minimization of methodologic bias in preclinical pain research: Precise considerations. Pain, 2016. 157(4): p. 901-9.

(56) References Cited

OTHER PUBLICATIONS

Chen, Z., et al., Disrupted functional connectivity of periaqueductal gray subregions in episodic migraine. J Headache Pain, 2017. 18(1): p. 36.
Buczynski, M.W., et al., Quantification of brain endocannabinoid levels: methods, interpretations and pitfalls. Br J Pharmacol, 2010. 160(3): p. 423-42.
Zoerner, A.A., et al., Quantification of endocannabinoids in biological systems by chromatography and mass spectrometry: A comprehensive review from analytical and biological perspective. Biochim Biophys Acta, 2011. 1811(11): p. 706-23.
Greco, R., et al., Alterations of the endocannabinoid system in an animal model of migraine: evaluation in cerebral areas of rat. Cephalgia, 2010. 30(3): p. 296-302.
Gentile, A., et al., Interaction between interleukin-1β and type-1 cannabinoid receptor is involved in anxiety-like behavior in experimental autoimmune encephalomyelitis. J Neuroinflammation, 2016. 13(1): p. 231.
Daigle, T.L., et al., Regulation of CB1 cannabinoid receptor internalization by a promiscuous phosphorylationdependent mechanism. J Neurochem, 2008. 106(1): p. 70-82.
Kingsley, P.J. and L.J. Marnett, Analysis of endocannabinoids, their congeners and COX-2 metabolites. J Chromatogr B Analyt Technol Biomed Life Sci, 2009. 877(26): p. 2746-54.
Kingsley, P.J., et al., Aspects of Prostaglandin Glycerol Ester Biology. Adv Exp Med Biol, 2019. 1161: p. 77-88.
Kudalkar, S.N., P.J. Kingsley, and L.J. Marnett, Assay of Endocannabinoid Oxidation by Cyclooxygenase-2. Methods Mol Biol, 2016. 1412: p. 205-15.
Morgan, A.J., et al., Detection of Cyclooxygenase-2-Derived Oxygenation Products of the Endogenous Cannabinoid 2-Arachidonoylglycerol in Mouse Brain. ACS Chem Neurosci, 2018. 9(7): p. 1552-1559.
Blancaflor, E.B., et al., N-Acylethanolamines: lipid metabolites with functions in plant growth and development. Plant J, 2014. 79(4): p. 568-83.
Keereetaweep, J., et al., Lipoxygenase-derived 9-hydro(pero)xides of linoleoylethanolamide interact with ABA signaling to arrest root development during Arabidopsis seedling establishment. Plant J, 2015. 82(2): p. 315-27.
Keereetaweep, J. and K.D. Chapman, Lipidomic Analysis of Endocannabinoid Signaling: Targeted Metabolite Identification and Quantification. Neural Plast, 2016. 2016: p. 2426398.
Reisenberg, M., et al., The diacylglycerol lipases: structure, regulation and roles in and beyond endocannabinoid signalling. Philos Trans R Soc Lond B Biol Sci, 2012. 367(1607): p. 3264-75.
Ignatowska-Jankowska, B.M., et al., In vivo characterization of the highly selective monoacylglycerol lipase inhibitor KML29: antinociceptive activity without cannabimimetic side effects. Br J Pharmacol, 2014. 171(6): p. 1392-407.
Niphakis, M.J., et al., Evaluation of NHS carbamates as a potent and selective class of endocannabinoid hydrolase inhibitors. ACS Chem Neurosci, 2013. 4(9): p. 1322-32.
Hsu, K.L., et al., Discovery and optimization of piperidyl-1,2,3-triazole ureas as potent, selective, and in vivo-active inhibitors of alpha/beta-hydrolase domain containing 6 (ABHD6). J Med Chem, 2013. 56(21): p. 8270-9.
Manterola, A., et al., Re-examining the potential of targeting ABHD6 in multiple sclerosis: Efficacy of systemic and peripherally restricted inhibitors in experimental autoimmune encephalomyelitis. Neuropharmacology, 2018. 141: p. 181-191.
Millan, M.J., Descending control of pain. Prog Neurobiol, 2002. 66(6): p. 355-474.
Sandweiss, A.J., et al., 17-beta-Estradiol induces spreading depression and pain behavior in alert female rats. Oncotarget, 2017. 8(69): p. 114109-114122.
Kiritoshi, T., G. Ji, and V. Neugebauer, Rescue of Impaired mGluR5-Driven Endocannabinoid Signaling Restores Prefrontal Cortical Output to Inhibit Pain in Arthritic Rats. The Journal of neuroscience : the official journal of the Society for Neuroscience, 2016. 36(3): p. 837-850.
Chen, Z., et al., Sphingosine-1-phosphate receptor 1 activation in astrocytes contributes to neuropathic pain. Proc Natl Acad Sci U S A, 2019. 116(21): p. 10557-10562.
Edwards, K.A., et al., A Kappa Opioid Receptor Agonist Blocks Bone Cancer Pain Without Altering Bone Loss, Tumor Size, or Cancer Cell Proliferation in a Mouse Model of Cancer-Induced Bone Pain. J Pain, 2018. 19(6): p. 612-625.
Largent-Milnes, T.M., et al., Building a Better Analgesic: Multifunctional Compounds that Address Injury-Induced Pathology to Enhance Analgesic Efficacy while Eliminating Unwanted Side Effects. Journal of Pharmacology and Experimental Therapeutics, 2013. 347(1): p. 7-19.
Largent-Milnes, T.M., et al., Oxycodone plus ultra-low-dose naltrexone attenuates neuropathic pain and associated mu-opioid receptor-Gs coupling. J Pain, 2008. 9(8): p. 700-13.
Marshall, T.M., et al., Activation of descending pain-facilitatory pathways from the rostral ventromedial medulla by cholecystokinin elicits release of prostaglandin-E(2) in the spinal cord. Pain, 2012. 153(1): p. 86-94.
Thompson, A.L., T.M. Largent-Milnes, and T.W. Vanderah, Animal Models for the Study of Bone-Derived Pain. Methods Mol Biol, 2019. 1914: p. 391-407.
Vanderah, T.W., et al., Novel D-amino acid tetrapeptides produce potent antinociception by selectively acting at peripheral kappa-opioid receptors. Eur J Pharmacol, 2008. 583(1): p. 62-72.
Zhang, H., et al., Peripherally restricted cannabinoid 1 receptor agonist as a novel analgesic in cancer-induced bone pain. Pain, 2018. 159(9): p. 1814-1823.
Mechoulam, R., et al., Identification of an endogenous 2-monoglyceride, present in canine gut, that binds to cannabinoid receptors. Biochem Pharmacol, 1995. 50(1): p. 83-90.
Sugiura, H., et al., Role of peroxynitrite in airway microvascular hyperpermeability during late allergic phase in guinea pigs. American Journal of Respiratory and Critical Care Medicine, 1999. 160(2): p. 663-671.
Sugiura, T., et al., Evidence that 2-arachidonoylglycerol but not N-palmitoylethanolamine or anandamide is the physiological ligand for the cannabinoid CB2 receptor. Comparison of the agonistic activities of various cannabinoid receptor ligands in HL-60 cells. J Biol Chem, 2000. 275(1): p. 605-12.
Diaz, P., et al., Design and synthesis of a novel series of N-alkyl isatin acylhydrazone derivatives that act as selective cannabinoid receptor 2 agonists for the treatment of neuropathic pain. J Med Chem, 2008. 51(16): p. 4932-47.
Fang, Q., et al., Effects of neuropeptide FF system on CB(1) and CB(2) receptors mediated antinociception in mice. Neuropharmacology, 2012. 62(2): p. 855-64.
Ledent, C., et al., Unresponsiveness to cannabinoids and reduced addictive effects of opiates in CB1 receptor knockout mice. Science, 1999. 283(5400): p. 401-4.
Naguib, M., et al., MDA7: a novel selective agonist for CB2 receptors that prevents allodynia in rat neuropathic pain models. Br J Pharmacol, 2008. 155(7): p. 1104-16.
Rahn, E.J., A. Makriyannis, and A.G. Hohmann, Activation of cannabinoid CB1 and CB2 receptors suppresses neuropathic nociception evoked by the chemotherapeutic agent vincristine in rats. Br J Pharmacol, 2007. 152(5): p. 765-77.
Ryberg, E., et al., The orphan receptor GPR55 is a novel cannabinoid receptor. Br J Pharmacol, 2007. 152(7): p. 1092-101.
Cheer, J.F., et al., Cannabinoids enhance subsecond dopamine release in the nucleus accumbens of awake rats. J Neurosci, 2004. 24(18): p. 4393-400.
Kargl, J., et al., A Selective Antagonist Reveals a Potential Role of G Protein-Coupled Receptor 55 in Platelet and Endothelial Cell Function. Journal of Pharmacology and Experimental Therapeutics, 2013. 346(1): p. 54.
AlSuleimani, Y.M. and C.R. Hiley, The GPR55 agonist lysophosphatidylinositol relaxes rat mesenteric resistance artery and induces Ca(2+) release in rat mesenteric artery endothelial cells. Br J Pharmacol, 2015. 172(12): p. 3043-57.

(56) References Cited

OTHER PUBLICATIONS

Bouchard, J., et al., Cannabinoid receptor 2 signaling in peripheral immune cells modulates disease onset and severity in mouse models of Huntington's disease. The Journal of neuroscience : the official journal of the Society for Neuroscience, 2012. 32(50): p. 18259-18268.

Grenald, S.A., et al., Targeting the S1P/S1PR1 axis mitigates cancer-induced bone pain and neuroinflammation. Pain, 2017. 158(9): p. 1733-1742.

Moutal, A., et al., Cdk5-mediated CRMP2 phosphorylation is necessary and sufficient for peripheral neuropathic pain. Neurobiol Pain, 2019. 5.

Wilkerson, J.L., et al., The Selective Monoacylglycerol Lipase Inhibitor MJN110 Produces Opioid-Sparing Effects in a Mouse Neuropathic Pain Model. J Pharmacol Exp Ther, 2016. 357(1): p. 145-56.

Naydenov A.V., et al., ABHD6 blockade exerts antiepileptic activity in PTZ-induced seizures and in spontaneous seizures in R6/2 mice. Neuron, 2014. 83(2): 361-371.

* cited by examiner

FIG. 2A-D
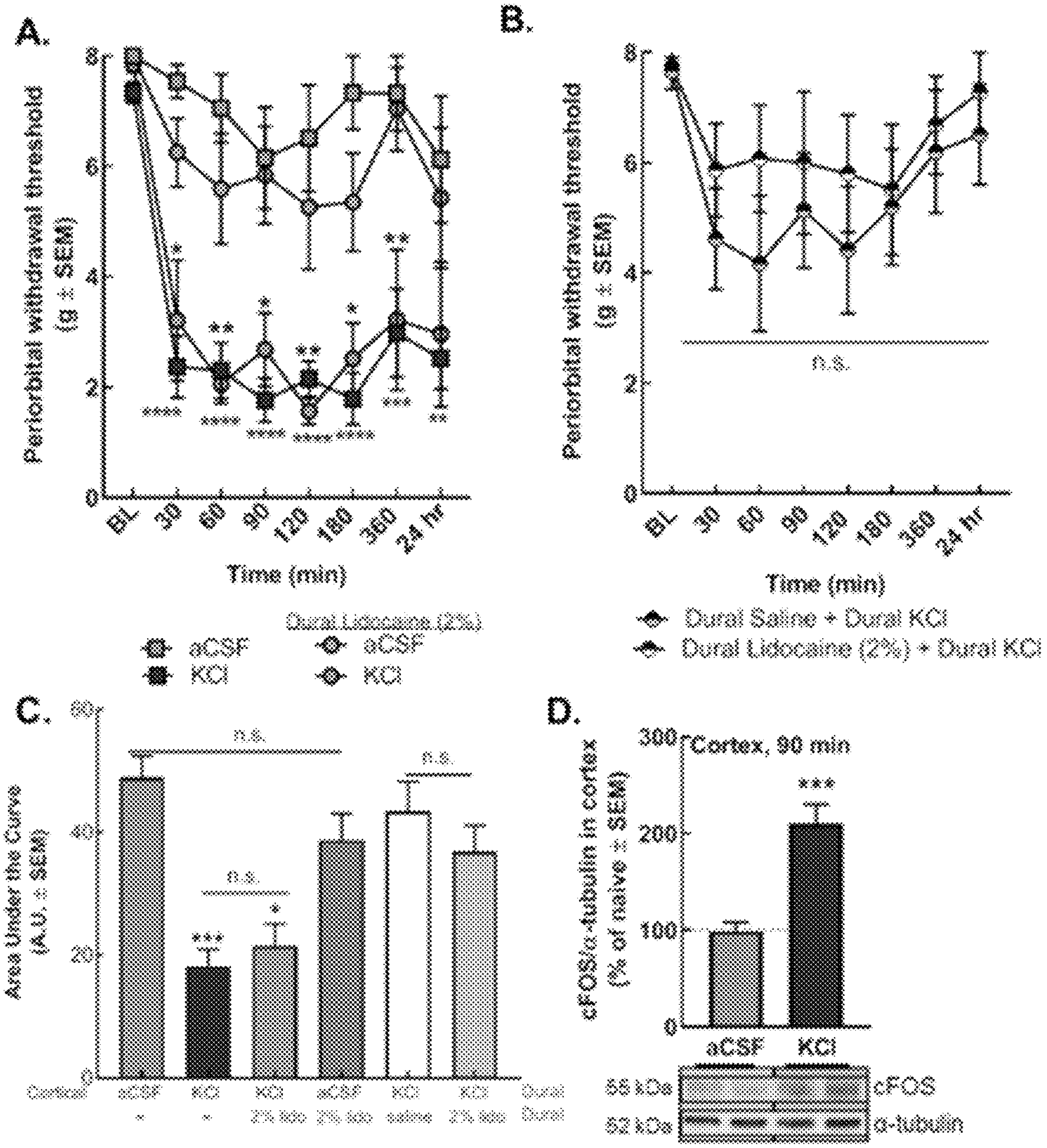

FIG. 3A-F
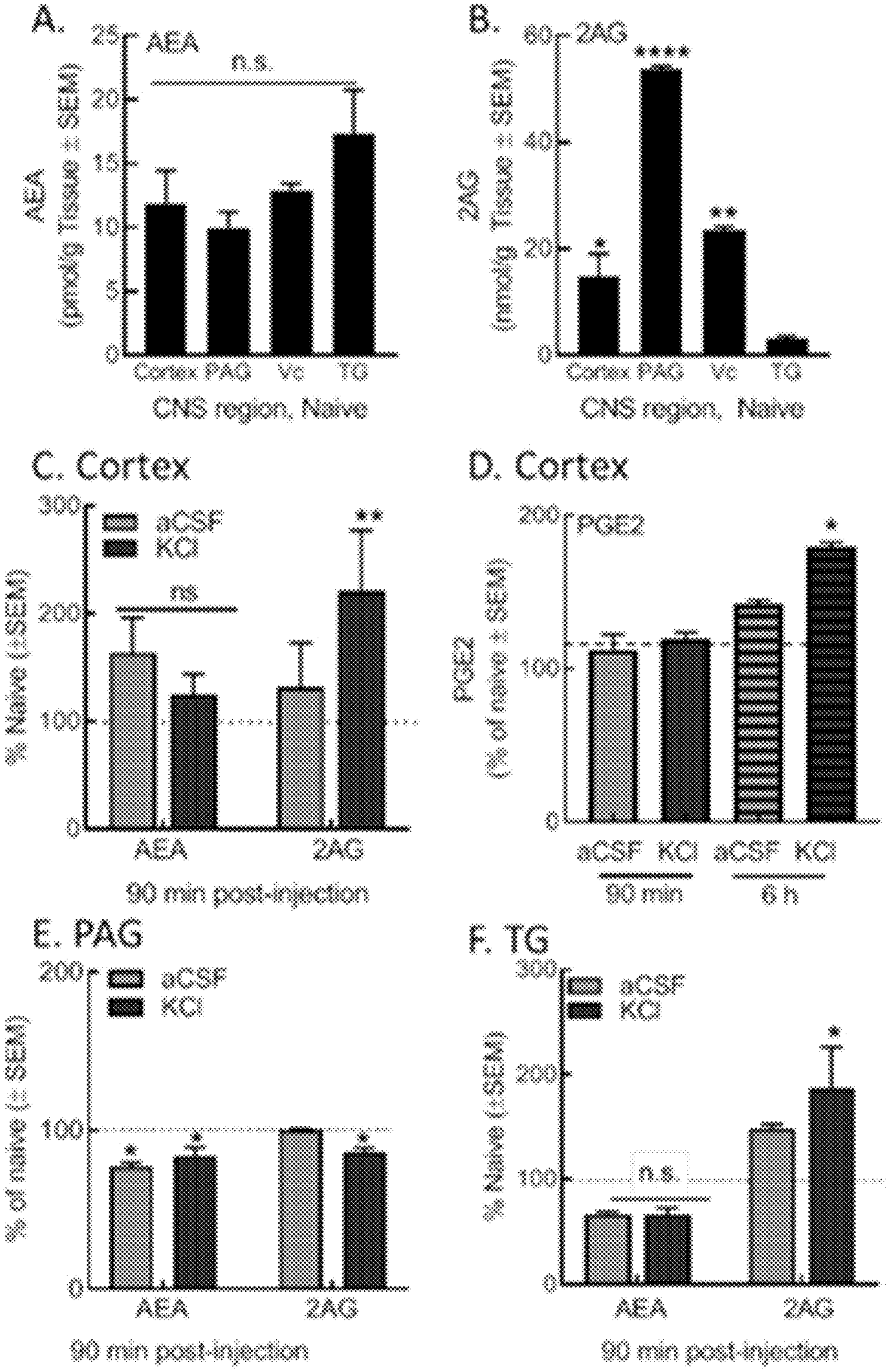

FIG. 4A-B
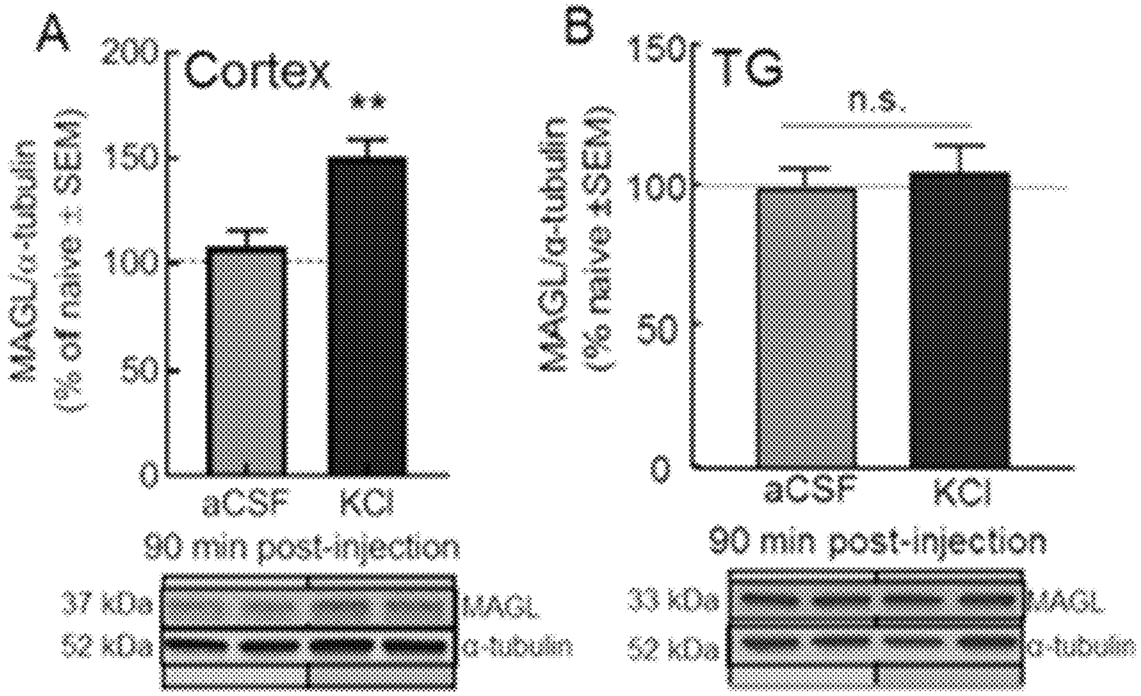
FIG. 5A-C
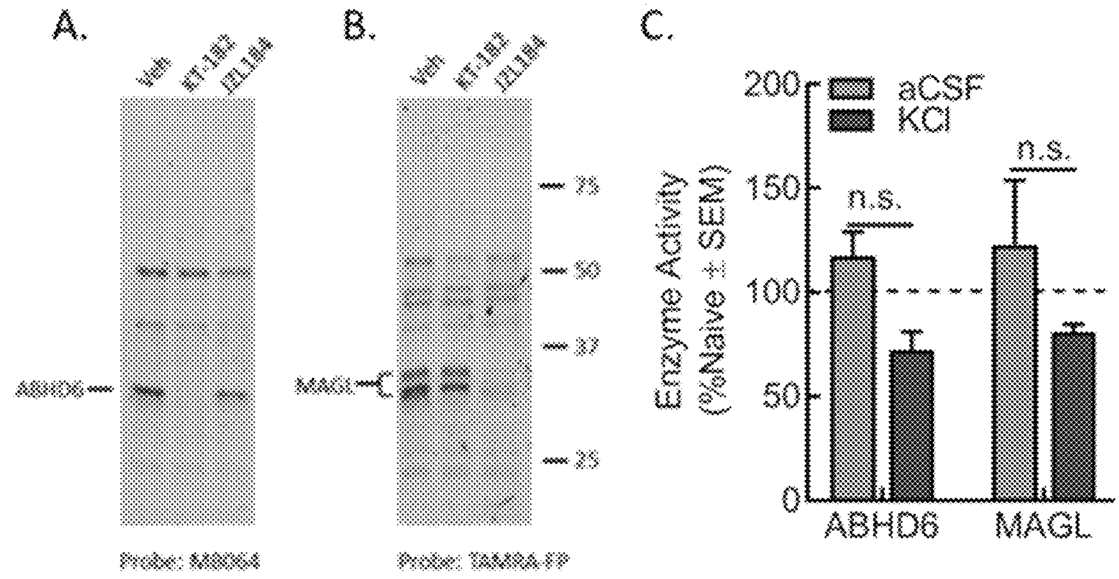

FIG. 6A-C
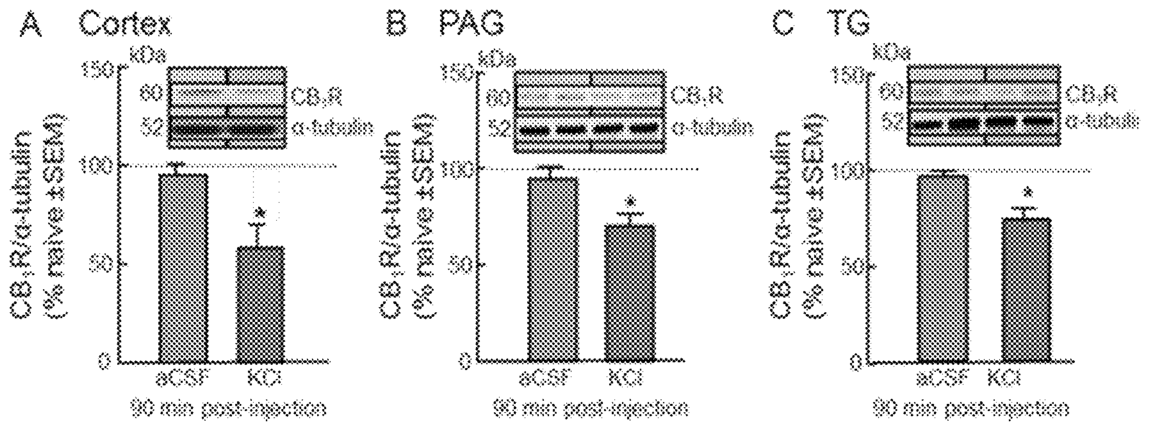
FIG. 7A-D
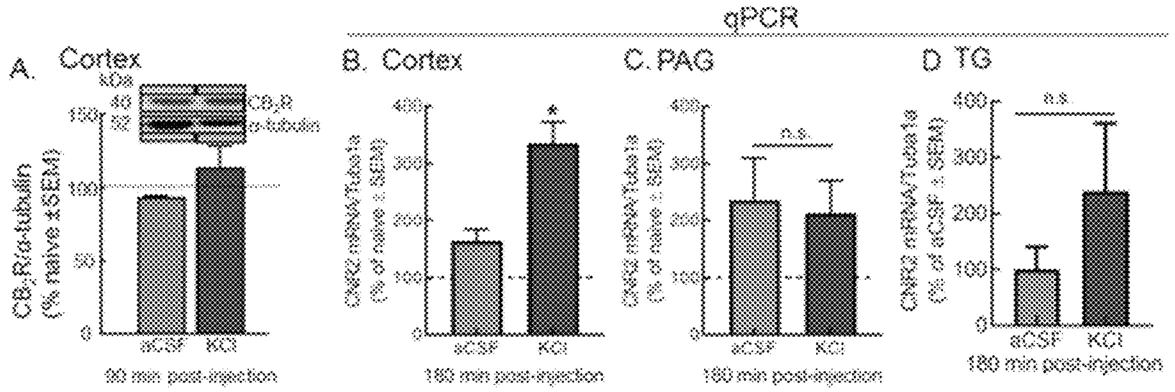

FIG. 8A-B
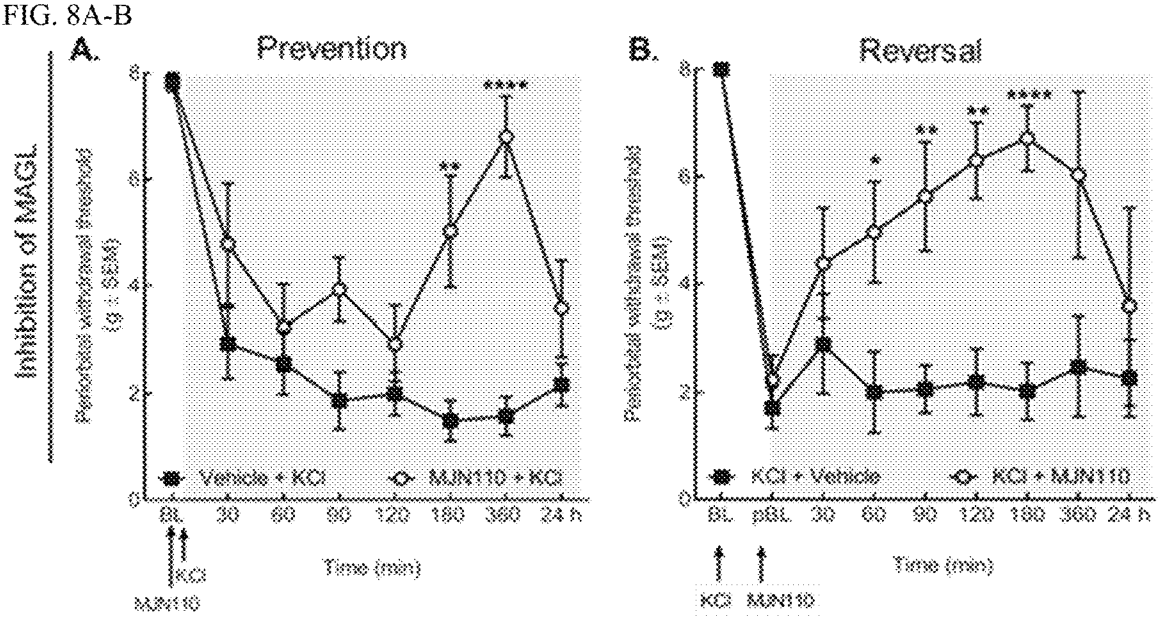
FIG. 9A-B
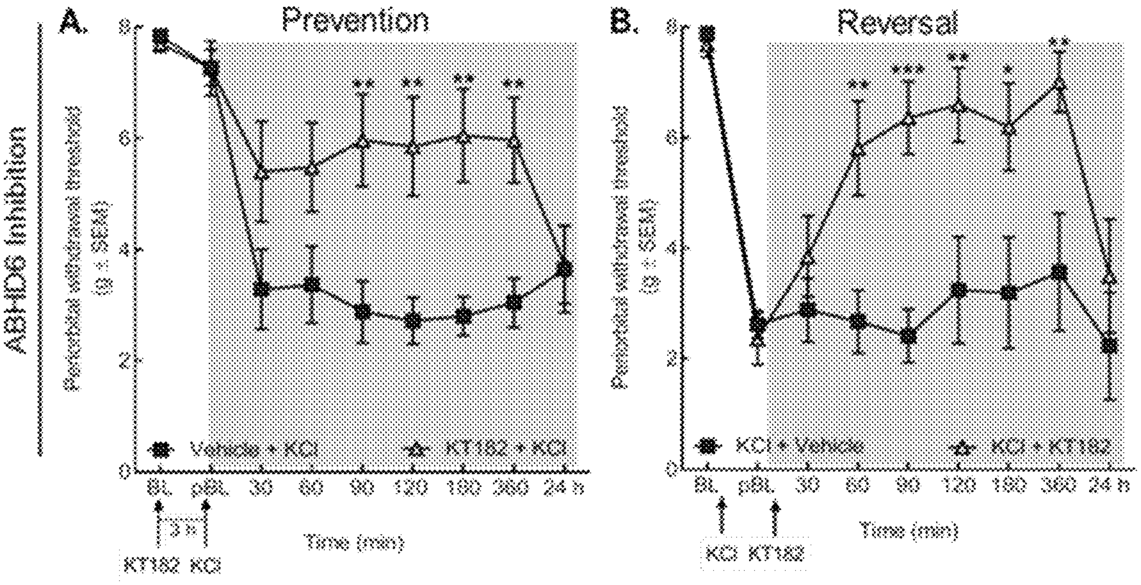

FIG. 10A-B
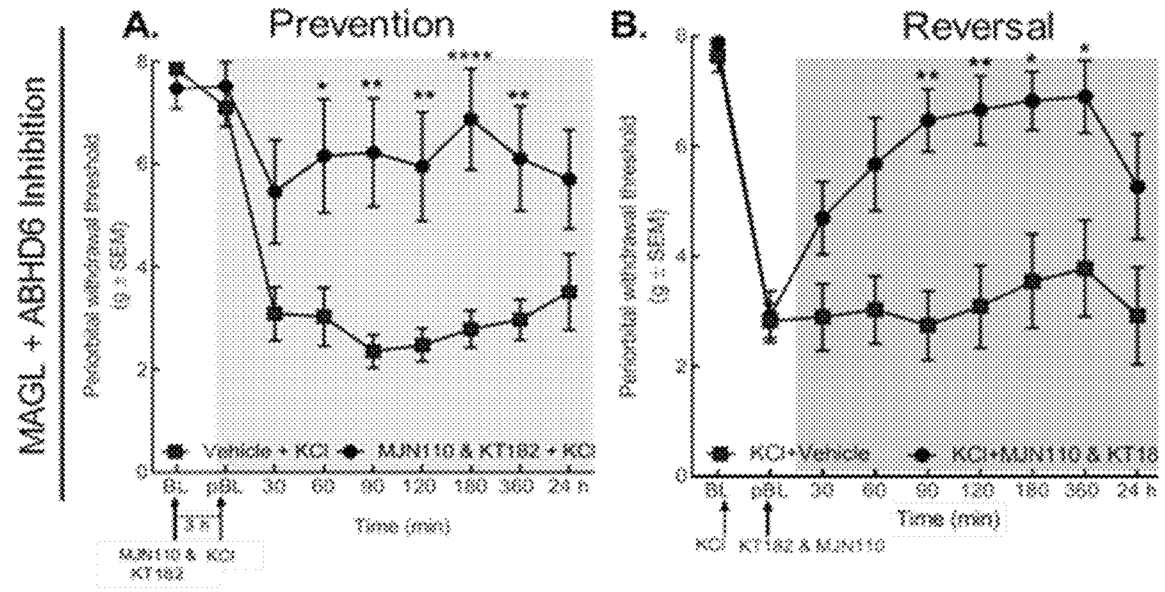
FIG. 11A-B
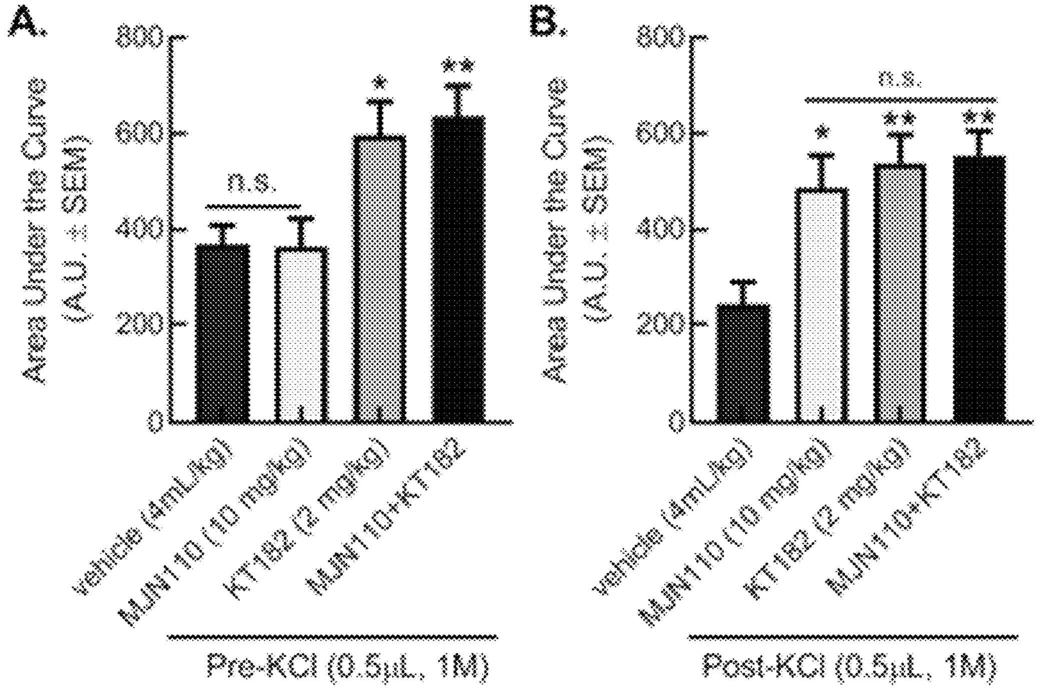

FIG. 12
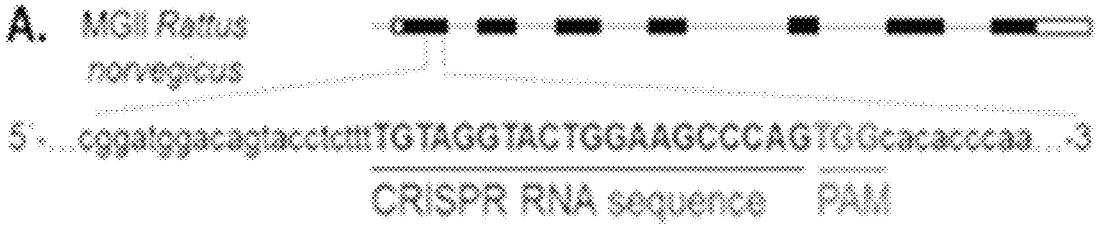
(SEQ ID NO: 1)
FIG. 13A-B
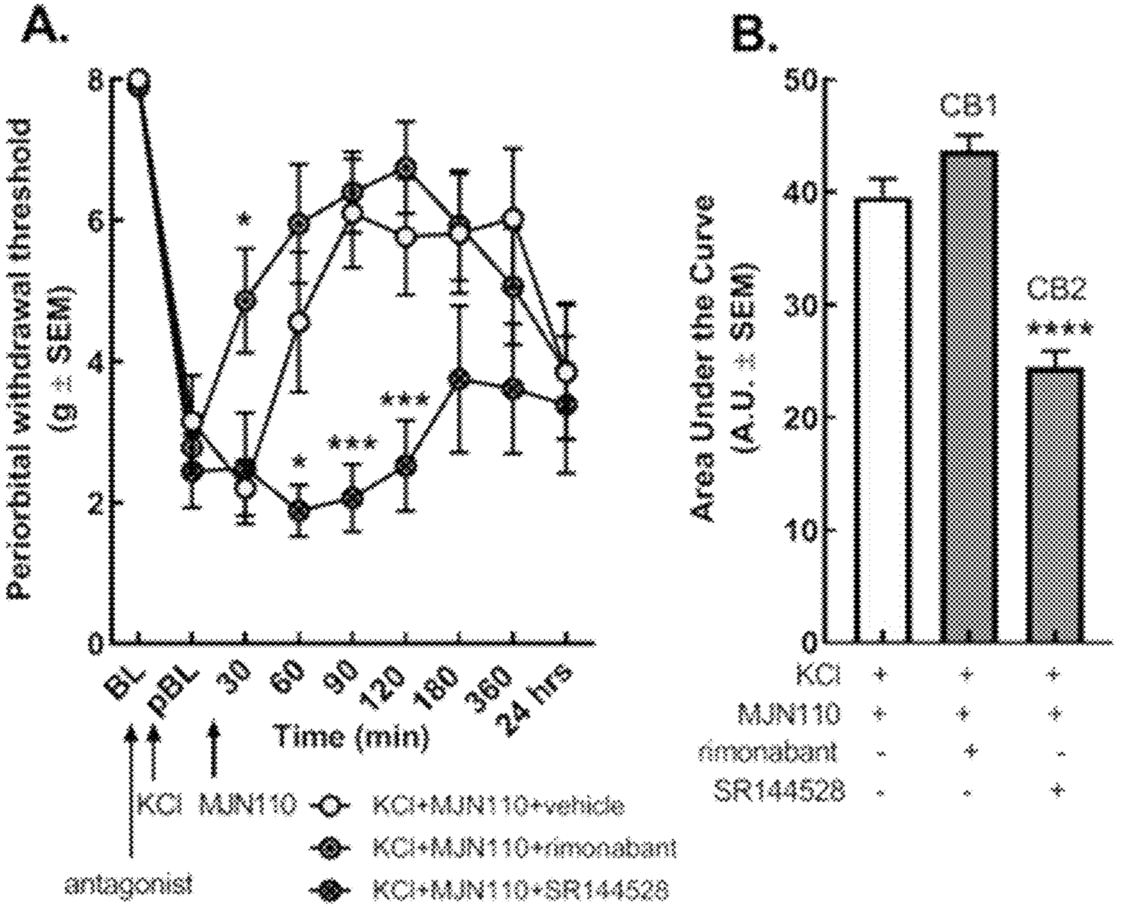

COMPOSITIONS AND METHODS FOR PREVENTING AND TREATING HEADACHE THROUGH ENHANCING 2-ARACHYDONYL GLYEROL ACTIVITY

CROSS-REFERENCE TO RELATED APPLICATION

This application claims priority to U.S. Provisional Patent Application No. 63/032,183 filed May 29, 2020, the contents of which are incorporated by reference in its entirety.

STATEMENT REGARDING FEDERALLY SPONSORED RESEARCH OR DEVELOPMENT

This invention was made with government support under Grant No. R01 DA026430 awarded by National Institutes of Health. The government has certain rights in the invention.

FIELD OF THE INVENTION

This invention relates generally to compositions and methods for preventing, reducing the occurrence of or treating a headache in a subject in need thereof. In particular, the present invention relates to methods for enhancing 2-arachydonyl glycerol (2AG) tone and reducing prostaglandin activity in a subject for purposes of preventing, reducing the occurrence of or treating a headache (e.g., a migraine headache) in a subject.

BACKGROUND OF THE INVENTION

A headache is a pain in the head, such as in the scalp, face, forehead or neck. Tension headache is the most common type of primary headache and tension headaches account for about 90% of all headaches. A tension headache is often experienced in the forehead, in the back of the head and neck, or in both regions. It has been described as a tight feeling, as if the head were in a vise. Soreness in the shoulders or neck is common. Nausea is uncommon with a tension headache. Migraine headaches are recurrent headaches that may be unilateral or bilateral. Migraine headaches may occur with or without a prodrome. The aura of a migraine may consist of neurologic symptoms, such as dizziness, tinnitus, scotomas, photophobia, or visual scintillations (e.g., bright zigzag lines). Migraines without aura are the most common, accounting for more than 80% of all migraines. An estimated 10-20% of the population suffers from migraine headaches. An estimated 6% of men and 15-17% of women in the United States have migraine. Migraines most commonly are found in women, with a 3:1 female-to-male ratio.

Migraine is one of the most common, yet under studied, neurological syndrome, contributing to the 116 million Americans (14.2% of US adults) experiencing chronic pain. The complex symptoms of migraine include intense headache, disturbed vision, vomiting, and sensitivity to light, sound and smell.

The variety of pharmacologic interventions that have been used to treat migraine and the variability in responses among patients are a testament to the diverse nature of this disorder. Thus, such relatively non-selective drugs as ergot alkaloids (e.g., ergotamine, dihydroergotamine, methysergide), which exhibit serotonergic, as well as adrenergic, noradrenergic and dopaminergic activity, have been used for over eighty years to treat migraine. Other treatments include opiates (e.g., oxycodone) and 3-adrenergic antagonists (e.g., propranolol). Some patients, usually those with milder symptoms, are able to control their symptoms with non-prescription remedies such as one or more non-steroidal anti-inflammatory agents (NSAIDs), such as a combination of aspirin, acetaminophen and caffeine (e.g., Excedrin.RTM. Migraine).

More recently, some migraine patients have been treated with topiramate, an anticonvulsant that blocks voltage-dependent sodium channels and certain glutamate receptors (AMPA-kainate), potentiates GABA-A receptor activity, and blocks carbonic anhydrase. The relatively recent success of serotonin 5HT-1B/1D and/or 5HT-la receptor agonists, such as sumatriptan, in some patients has led researchers to propose a serotonergic etiology of the disorder. Unfortunately, while some patients respond well to this treatment, others are relatively resistant to its effects.

Despite a large prevalence and severe symptoms, there are few antimigraine therapeutic strategies with moderate effectiveness, limited tolerability, and serious longterm side-effects.

As such, improved methods are needed for preventing, reducing the occurrence of or treating headaches and headache related pain.

The present invention addresses this need.

BRIEF DESCRIPTION OF THE DRAWINGS

FIG. 2A-D: Cortical KCl, but not dural KCl, induces periorbital allodynia in female rats and activates cFOS. A. Cortical KCl (0.5 µL, 1M) induces significant periorbital allodynia that is not blocked by dural lidocaine (2%, 5 µl, 10-15 min) pretreatment. B. Dural stimulation with KCl (5 uL, 1M) does not induce significant periorbital allodynia: lidocaine pretreatment showed no effect. C. Comparing areas under the curves for A and B confirmed that cortical KCl, regardless of dural lidocaine, induces significant periorbital allodynia that is not replicated by dural application of KCl. D. Cortical KCl allodynia increases cortical cFos 90 min post-injection (n=3-4/group). Data are mean±SEM (n=8-11), one or two-way ANOVA, *p<0.05: <0.01: *p<0.001: dotted line-naïve.

FIG. 3A-F: 2AG, but not AEA levels, were altered after cortical KCl in region-specific manner. Regional differences were observed in the level of 2AG, but not AEA in naïve samples (Cortex, PAG, Vc, and TG) (A and B). Cortical KCl injection, but not aCSF, increased the level of 2AG in cortex (C), resulting increased PGE2, a principal mediator of inflammation (D). 2AG decreased in PAG (E) but elevated in TG samples (F) 90 after cortical KCl injection. Data are given as mean±SEM (n=4-7), one-way ANOVAs, *p<0.05, **p<0.01. Dotted line-naïve.

FIGS. 4A-B: MAGL expression in A. Cortex and B. TG 90 min after cortical aCSF or KCl. Cortical KCl significantly increased MAGL expression in Cortex but not in the TG. Data are expressed as mean±SEM (n=4-7), one-way ANOVA, **p<0.01: Dotted line=naïve.

FIG. 5A-C: Expression/activity of ABHD6 (A) and MAGL (B) in naïve rat Cortex using 300 nM KT182 or 3 uM JZL184 (30 min, 37° C.) followed by 500 nM TAMRA-FP and 250 nM MB064 (15 min 37° C.). (C) Enzyme activity of both ABHD6 and MAGL in Cortex were statistically unaffected by cortical aCSF or KCl (ABHD6 p=0.06: MAGL p=0.34: One-way ANOVA) n=3/condition.

FIG. 6A-C: CB1R protein expression is reduced 90 min after cortical KCl in Cortex (A), PAG (B), and TG (C) but not following aCSF as compared to Naïve one-way ANOVA *$p<0.05$. Data are shown as Mean+/−SEM. n=3/treatment.

FIG. 7A-D: CB2R Expression. A. Protein levels of CB2R were assessed 90 min postaCSF/KCl injection: no significant changes as compared to naïve were observed. Given the variability in CB2R antibodies, we then evaluated mRNA expression of the CB2 gene CNR2. CNR2 mRNA is increased 180 min after cortical KCl in Cortex (B) but not in the PAG (C) or TG (D) suggesting dynamic changes in the ECS in this model, one-way ANOVA (n=3/treatment), *$p<0.05$. Data are mean+/−SEM.

FIG. 8A-B: MAGL inhibition alleviates cortical KCl induced periorbital allodynia in female rats. Injection of MJN110 (10 mg/kg, IP) before or after cortical KCl (IM, 0.5 μL) significantly (A) prevents and (B) reverses periorbital allodynia. Data are expressed mean±SEM (n=8-12), two-way RMANOVA Bonferroni, *$p<0.051$ $p<0.01$: **$p<0.0001$.

FIG. 9A-B: ABHD6 inhibition alleviates cortical KCl induced periorbital allodynia in female rats. Injection of KT182 (2 mg/kg. IP) before or after cortical KCl (IM, 0.5 μL) significantly prevents (A) and reverses (B) periorbital allodynia. Data are expressed mean±SEM (n=8-12), two-way RMANOVA Bonferroni, *$p<0.05$: $p<0.01$: *$p<0.001$.

FIG. 10A-B: Dual MAGL/ABHD6 inhibition alleviates cortical KCl induced periorbital allodynia in female rats. Co-injection of MJN (10 mg/kg IP) with KT182 (2 mg/kg, IP) before or after cortical KCl (IM, 0.5 μL) significantly prevents (A) and reverses (B) facial allodynia. Data are expressed mean±SEM (n=7-14), two-way RMANOVA, Bonferroni, *$p<0.05$: $p<0.01$: **$p<0.0001$.

FIG. 11A-B: AUCs for vehicle, MJN110 (10 mg/kg IP), KT182 (2 mg/kg, IP), and co-injected MJN110 & KT182 before (A) or after (B) cortical KCl (IM, 0.5 μL) Data are expressed mean±SEM (n=7-14), one-way ANOVA Bonferroni, *$p<0.05$, **$p<0.01$.

FIG. 12: A schematic of the Cas9/sgRNA system targeting the first exon of MGll (monoacylglycerol lipase gene).

FIG. 13A-B: MAGL inhibition and cannabinoid receptor selectivity. Injection of CB1R antagonist, rimonabant (1 mg/kg, IP) prior to KCl shifted onset of MJN110 (10 mg/kg, IP) by 30 min. CB2R antagonist, SR144528 (1 mg/kg, IP), injected prior to KCl blocked the anti-allodynic effect of MJN110. Data are expressed mean±SEM (n=9), one- and two-way ANOVA, *$p<0.05$, *$p<0.001$, **$p<0.0001$.

SUMMARY

Figure 1:
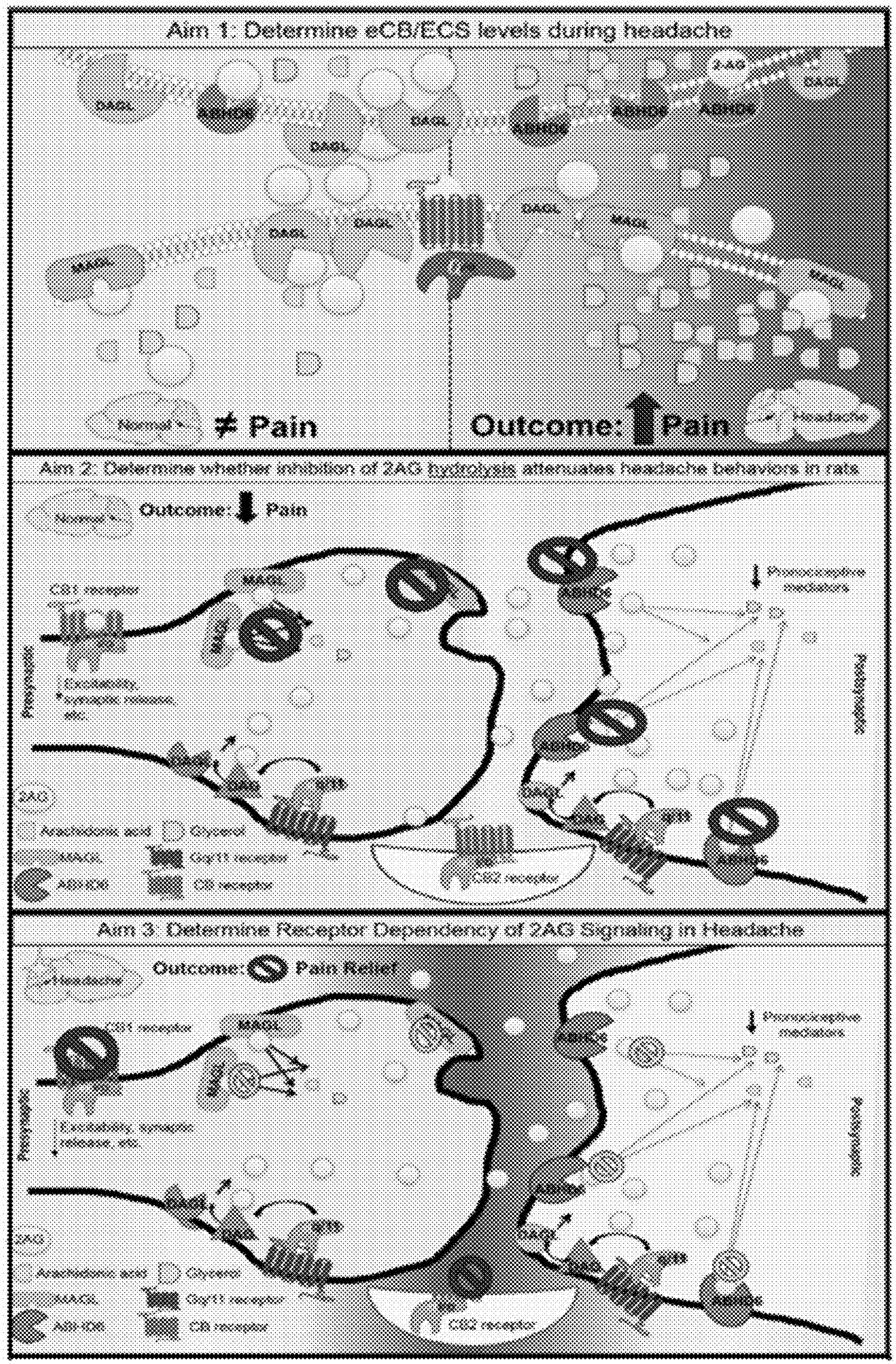
FIG. 1: Summary of specific aims of the experiments described in Example I.

The endocannabinoid system (ECS) recently received attention linking attenuation of pain, including migraine, to endocannabinoid signaling. Components of the endocannabinoid system include the bioactive lipid compounds named endocannabinoids (eCB), their metabolic enzymes (e.g., mono- and di-acyl glycerol lipase, MAGL and DAGL, serine hydrolase ABHD6, serine hydrolase ABHD12), and their receptors, the CB1 and CB2. Recent clinical experiments support the idea of Endocannabinoid Deficiency (CED) as a potential mechanism of migraine in patients. However biochemical studies providing strong evidence for the potential efficacy of eCBs in migraine are limited. Indeed, prior to the experiments described herein, no study has investigated the changes in levels and function of each ECS component in headache. Experiments conducted during the course of developing embodiments for the present invention tackled this major gap in migraine pathology by elucidating the role of endocannabinoids in migraine, using an integrated approach of analytical chemistry, molecular biology, systems neuropharmacology and functional expression analyses.

Monoacylglycerol lipase (MAGL), ABHD6 and ABHD12 are key enzymes in the hydrolysis of the endocannabinoid, 2-arachidonoylglycerol (2-AG), whereas DAGL is the major enzyme generating 2-AG in the central nervous system. Such experiments indicated that overactivity of MAGL and loss of DAGL expression in regionally distinct areas of the trigeminal pain axis with temporal dynamics following cortical injection of KCl. Experiments were conducted with the postulation that pathogenic remodeling of the 2AG endocannabinoid signaling system plays a critical role in the generation of headache pain that can be targeted therapeutically. It was shown that increasing eCB tone by targeting either MAGL, ABHD6, and/or ABHD12 as an effective strategy for headache therapy (e.g., migraine therapy). Such experiments resulted in the discovery that endogenous 2AG levels in four discrete nuclei associated with headache (e.g., cortex, periaqueductal grey-PAG, trigeminal nucleus caudalis-Vc, and the trigeminal ganglia-TG) are regionally regulated over time as a result of decreases in DAGL functional expression (TG) and increases in 2AG degradation by MAGL and ABHD6 (Cortex, PAG). Moreover, it was shown that induction of facial allodynia confers a shift in 2AG signaling away from CB1R. Importantly, such experiments demonstrated that inhibition of MAGL and ABHD6 profoundly attenuated periorbital allodynia occurring after cortical KCl injection and indicated unique roles for MAGL and ABHD6 in reversal and prevention of facial sensitivity, respectively. As such, such experiments indicate that induction of headache pain results from enhanced degradation of 2AG by MAGL and ABHD6 that can be targeted pharmaceutically.

As such, this invention relates generally to compositions and methods for preventing, reducing the occurrence of or treating a headache in a subject in need thereof. In particular, the present invention relates to methods for enhancing 2-arachydonyl glycerol (2AG) tone and reducing prostaglandin activity in a subject for purposes of preventing, reducing the occurrence of or treating a headache (e.g., a migraine headache) in a subject.

In certain embodiments, the present invention provides a method of preventing, reducing the occurrence of or treating a headache in a mammal comprising administering to the mammal a pharmaceutical composition capable of enhancing 2AG tone in the mammal.

In certain embodiments, the present invention provides a method of preventing, reducing the occurrence of or treating a headache in a mammal comprising administering to the mammal a pharmaceutical composition capable of inhibiting prostaglandin activity in the mammal.

In certain embodiments, the present invention provides a method of preventing, reducing the occurrence of or treating a headache in a mammal comprising administering to the mammal a pharmaceutical composition capable of enhancing 2AG tone and inhibiting prostaglandin activity in the mammal.

Such methods are not limited to a particular type of mammal. In some embodiments, the mammal is a human being. In some embodiments, the mammal is a human being suffering from or at risk of suffering from a headache (e.g., a migraine headache).

Such methods are not limited to treating a particular type or kind of headache. In some embodiments, the headache is a non-migraine headache. In some embodiments, the headache is a migraine headache. In some embodiments, the migraine headache is a chronic migraine headache. In some embodiments, the headache is an episodic migraine headache.

Such methods are not limited to a particular type of pharmaceutical composition capable of enhancing 2AG tone and/or reducing prostaglandin activity in the mammal.

In some embodiments, the pharmaceutical composition capable of enhancing 2AG tone and/or reducing prostaglandin activity in the mammal comprises an agent capable of inhibiting MAGL expression and/or activity levels. In some embodiments, the agent capable of inhibiting MAGL expression and/or activity levels is MJN110 (e.g.,

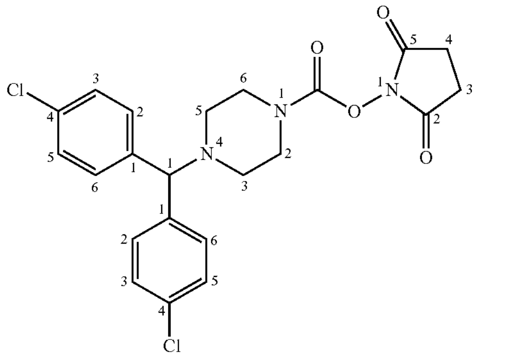 [SMILES: O=C(ON1C(=O)CCC1=O)N1CCN(C(c2ccc(Cl)cc2)c2ccc(Cl)cc2)CC1]

2,5-dioxopyrrolidin-1-yl 4-(bis(4-chlorophenyl)methyl) piperazine-1-carboxylate). In some embodiments, the agent capable of inhibiting MAGL expression and/or activity levels is structurally similar to MJN110. In some embodiments, the agent capable of inhibiting MAGL expression and/or activity levels is small molecule. In some embodiments, the agent capable of inhibiting MAGL expression and/or activity levels is peptide. In some embodiments, the agent capable of inhibiting MAGL expression and/or activity levels is an antibody.

In some embodiments, the pharmaceutical composition capable of enhancing 2AG tone and/or reducing prostaglandin activity in the mammal comprises an agent capable of inhibiting ABHD6 expression and/or activity levels. In some embodiments, the agent capable of inhibiting

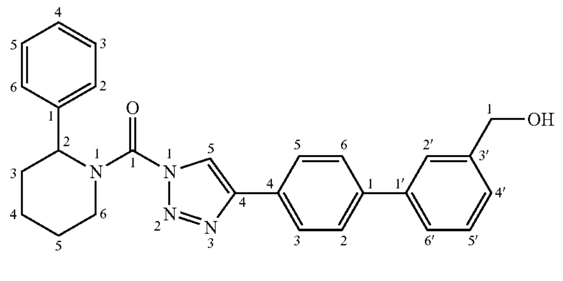

(4-(3'-(hydroxymethyl)-[1,1'-biphenyl]-4-yl)-1H-1,2,3-triazol-1-yl)(2-phenylpiperidin-1-yl) methanone). In some embodiments, the agent capable of inhibiting ABHD6 expression and/or activity levels is structurally similar to KT182. In some embodiments, the agent capable of inhibiting ABHD6 expression and/or activity levels is small molecule. In some embodiments, the agent capable of inhibiting ABHD6 expression and/or activity levels is peptide. In some embodiments, the agent capable of inhibiting ABHD6 expression and/or activity levels is an antibody.

In some embodiments, the pharmaceutical composition capable of enhancing 2AG tone and/or reducing prostaglandin activity in the mammal comprises an agent capable of inhibiting ABHD12 expression and/or activity levels. In some embodiments, the agent capable of inhibiting ABHD12 expression and/or activity levels is small molecule. In some embodiments, the agent capable of inhibiting ABHD12 expression and/or activity levels is peptide. In some embodiments, the agent capable of inhibiting ABHD12 expression and/or activity levels is an antibody.

In some embodiments, the pharmaceutical composition capable of enhancing 2AG tone and/or reducing prostaglandin activity in the mammal comprises an agent capable of enhancing DAGL expression and/or activity levels. In some embodiments, the agent capable of enhancing DAGL expression and/or activity levels is small molecule. In some embodiments, the agent capable of enhancing DAGL expression and/or activity levels is peptide. In some embodiments, the agent capable of enhancing DAGL expression and/or activity levels is an antibody.

In some embodiments, the pharmaceutical composition capable of enhancing 2AG tone and/or reducing prostaglandin activity in the mammal comprises one or more of the following agents: an agent capable of inhibiting MAGL activity and/or expression (e.g., MJN110), an agent inhibiting ABHD12 activity and/or expression, and an agent capable of enhancing DAGL activity and/or expression.

In some embodiments, the pharmaceutical composition capable of enhancing 2AG tone and/or reducing prostaglandin activity in the mammal comprises MJN110 and KT182.

In some embodiments, the methods further comprise co-administration of a pharmaceutical composition comprising a second agent (e.g., 5-HT1 agonists, triptans, ergot alkaloids, and non-steroidal anti-inflammatory drugs).

In certain embodiments, the present invention provides a method of enhancing 2AG tone and/or inhibiting prostaglandin activity in a mammal, comprising administering to the subject an agent capable of inhibiting MAGL expression and/or activity levels. In some embodiments, the agent capable of inhibiting MAGL expression and/or activity levels is MJN110.

In certain embodiments, the present invention provides a method of enhancing 2AG tone and/or inhibiting prostaglandin activity in a mammal, comprising administering to the subject an agent capable of inhibiting ABHD6 expression and/or activity levels. In some embodiments, the agent capable of inhibiting ABHD6 expression and/or activity levels is KT182.

In certain embodiments, the present invention provides a method of enhancing 2AG tone and/or inhibiting prostaglandin activity in a mammal, comprising administering to the subject an agent capable of inhibiting ABHD12 expression and/or activity levels.

In certain embodiments, the present invention provides a method of enhancing 2AG tone and/or inhibiting prostaglandin activity in a mammal, comprising administering to the subject an agent capable of enhancing DAGL expression and/or activity levels.

DETAILED DESCRIPTION

Migraine is characterized by severe headache, nausea and increased sensory sensitivity to light, sound and smell. This neurological syndrome is one of the most under studied disorders that affects 38 million individuals in the U.S. Remarkably, 5 million people experience at least one migraine attack per month, while more than 11 million migraineurs suffer from moderate to severe disability. Migraine leads to a loss in annual productivity of $6-17 billion [1, 2]. Adding to this grim picture, current therapies (i.e., triptans), reduce pain intensity and duration in only ~30% of patients [3]. Thus, the development of new therapeutics to mitigate and possible avoid migraine symptoms would have immediate clinical and socioeconomic benefits.

In addition to typical migraine symptoms of sensory sensitivity and pain, approximately ⅓ of patients with migraine experience focal neurological symptoms known as aura [4]. Auras vary between migraineurs and can include sensory, motor, verbal, auditory, or olfactory components and suggests a mechanism(s) linked to generalized cortical dysfunction. Cortical Spreading Depression (CSD, SD) is a self-propagating wave of membrane depolarization associated with aura that precedes the headache phase [5-7]. Though most frequently associated with migraine aura, CSDs have been linked to stroke (ischemic and hemorrhagic), traumatic brain injury, epilepsy, and multiple sclerosis, all of which are associated with secondary headache [8-11].

CSD events are initiated by a variety of stimuli, including electrical, mechanical, chemical, and metabolic [5-7, 9, 12-17]. Increases in extracellular K+ concentration from 3 mM to 55 mM are linked to changes in metabolism and intracellular homeostasis [7, 18-20]. For example, drops in brain pH may occur during prolonged aura associated with migraine [21], and the concomitant changes in Na+ homeostasis facilitate excitation of neurons and contractile cells of the CNS (i.e. vasculature smooth muscle). Overall, this rapid induction and decrease in synaptic transmission impairs intracellular signaling cascades. Though links between CSD, SD, and peri-infarct depressions events and headache have been postulated, mechanistic, causal evidence is still lacking. CSD events indirectly activate the trigeminal system leading to the release of vasoactive and pronociceptive neurotransmitters such as substance P, neurokinin A, and calcitonin gene-related peptide (CGRP) on the meninges [22, 23], culminating in trigeminovascular dysregulation. Dural inflammation can lead to mast cell recruitment and degranulation [24-27], dilatation of cerebral vasculature [28], and nociceptor and sympathetic fiber activation [14, 15, 27, 29] together producing headache [7,16]. A common feature of neuromodulator signaling implicated in migraine pathology (e.g., CGRP, PACAP, histamine, glutamate, bradykinin and ATP) is the engagement of Gaq/11 pathways [30-43]. G-protein coupled receptor (GPCR) activation of Gaq/11 signaling cascades produces inositol triphosphate (IP3) and diacylglycerol (DAG) from PIP2 via phospholipase C (PLC). This cascade enhances release of intracellular Ca2+ and downstream lipid signaling. The primary lipid generated from DAG is 2AG.

The endocannabinoid system (ECS) comprises two GPCRs (CB1R and CB2R), multiple lipid metabolizing enzymes, and the two main lipid mediators, anandamide and 2AG. Both CB1R and CB2R couple to second messenger pathways, including Gai and b-arrestins [44]. CB1R is expressed at high levels in the CNS and is mainly localized on presynaptic terminals [45-48]. CB2R is more frequently expressed on hematopoietic cells and mounting evidence suggest their role in regulation neurotransmission in brain [49-54]. Activation of both CB1R and CB2R relieves pain in preclinical model systems: though, they play divergent roles in reward liability [52, 53, 55-60]. CB1R and CB2R are activated by exogenous ligands, the most famous being THC, one of the main components of *Cannabis*.

The levels of lipid mediators are regulated by Ca2+ dependent enzymes and are thus often produced on-demand by activated cells: their inactivation occurs by transport and hydrolysis [37, 48, 61, 62]. AEA is synthesized from N-acylphosphatidylethanolamine by phospholipase D (NAPE-PLD) following cell activation (i.e. Ca2+ entry or release into cytosol). Once generated, AEA binds to and activates CB1R (Ki=61-543 nM: EC50)=1358 nM. Emax=64%) and CB2R (Ki=279-1,940 nM: EC50)=16 μM) [35, 63], as well as transient receptor potential channels (e.g., TRPV1) [41, 64]. AEA inactivation occurs via lipid binding proteins, passive diffusion across the membrane or carrier-mediated transport, and intracellular hydrolysis by fatty acid amide hydrolase (FAAH) [37, 65].

Synthesis and degradation of 2AG also occurs via multiple mechanisms. 2AG synthesis is largely performed by DAGL, which has two isoforms, a and B, with DAGLa isoform being prevalent in the brain [48]. Alternatively, 2AG is synthesized by PLAI from phosphatidyl lipid or by LPA hydrolysis [48]. 2AG activates CB1R (Ki=45-472 nM: EC50)=125.3 nM, Emax=100%) and CB2R (Ki=175-1,400 nM: EC50)=4 nM, 34% Emax) receptors and GPR55 (EC50)=618 nM) [48, 64, 66]. 2AG inactivation is mediated by MAGL and ABDH6, as well as additional enzymes depending on the pathophysiological state, for example ABHD12, cyclooxygenase, lipoxygenase and diacyl glycerol kinase-zeta [48]. FAAH can hydrolyze 2AG but this is observed in biochemical assays and not in vivo.

2AG hydrolysis by MAGL and ABHD6 is brain area and cell-type selective. MAGL is mainly presynaptic at extra synaptic regions rich in CB1R whereas ABHD6 primarily post-synaptic in dendrites [67, 68]. Both enzymes are expressed by glial cells. Given the expression profile of the ECS in brain, it is likely that disruptions in ligand synthesis, clearance/degradation, and/or receptor availability as a result of a pathological process may impair the proper physiology function of select brain areas.

Several studies suggested that the ECS is centrally and peripherally engaged during pain signaling [55, 69-74]. Recent clinical findings raised the idea that Clinical Endocannabinoid Deficiency (CED) syndrome underlies the pathophysiology of functional pain disorders, including migraine [75-77]. Patients, many of whom are female [78-81], with chronic migraine have reduced cerebrospinal fluid levels of AEA [75]: note that 2AG was not measured in this study. Patients suffering from chronic migraine or overusing headache medications showed reduced FAAH activity and ensuing increase in AEA levels [82, 83]. A possible role for impaired 2AG signaling with the ECS in these patients is unknown as its levels are below the limits of detection using current analytical methods, which should be emphasized since 2AG is typically present at concentrations >100-fold higher than AEA. Use of cannabis has proven effective in some migraine patients [84-88]: however, sustained use is associated with withdrawal headache or increases in migraine frequency [89, 90]. Preclinically, THC is effective in reducing migraine pain acutely [33, 91, 92] but repeated exposure increases migraine-like pain [33, 91-93]. This proposal will quantify 2AG levels in multiple brain regions associated with migraine to test its role in headache pain.

Initial evidence suggests ECS-dependent mechanisms underlying migraine and that activation of ECS, for example by increasing eCB tone with inhibitors of its hydrolyzing enzymes represents a powerful mechanistic approach to test its contributions and a promising therapeutic approach to reduce migraine [94]. For example, FAAH inhibitors dose dependently blocked nitroglycerine induced hyperalgesia, however the recent fatal failure of an FAAH inhibitor in Phase I clinical trial raises alarming questions about the safety of FAAH inhibitor class [95-97]. To date few studies exist on the beneficial role of a non-selective MAGL inhibitors in migraine besides studies using nitroglycerine administration [96, 98, 99] despite several studies proving the analgesic potential of MAGL inhibitors in other chronic pain conditions [98, 100]. Recent studies suggested that combined inhibition of FAAH and MAGL represents an analgesic strategy in multiple rodent models [69, 101-104] including dental pain [105]: that involves the PAG to modulate synaptic relay in sensory and motor systems [103, 106-108]. To date, Greco et al propose MAL as a therapeutic approach for headache pain [98]. Thus, no studies have evaluated the effect of ABHD6 inhibition and of dual ABHD6-MAGL inhibition in the context of migraine intervention. Given the unique expression pattern of these enzymes, experiments conducted during the course of developing embodiments for the present invention assessed the effect of inhibiting MAGL and ABHD6 alone and in combination on 2AG levels and on the pain response in preclinical models of migraine.

Experiments conducted during the course of developing embodiments for the present invention tackled this major gap in migraine pathology by elucidating the role of endocannabinoids in migraine, using an integrated approach of analytical chemistry, molecular biology, systems neuropharmacology and functional expression analyses.

Monoacylglycerol lipase (MAGL), ABHD6 and ABHD12 are key enzymes in the hydrolysis of the endocannabinoid, 2-arachidonoylglycerol (2-AG), whereas DAGL is the major enzyme generating 2-AG in the central nervous system. Such experiments indicated that overactivity of MAGL and loss of DAGL expression in regionally distinct areas of the trigeminal pain axis with temporal dynamics following cortical injection of KCl. Experiments were conducted with the postulation that pathogenic remodeling of the 2AG endocannabinoid signaling system plays a critical role in the generation of headache pain that can be targeted therapeutically. It was shown that increasing eCB tone by targeting either MAGL, ABHD6, and/or ABHD12 as an effective strategy for headache therapy (e.g., migraine therapy). Such experiments resulted in the discovery that endogenous 2AG levels in four discrete nuclei associated with headache (e.g., cortex, periaqueductal grey-PAG, trigeminal nucleus caudalis-Vc, and the trigeminal ganglia-TG) are regionally regulated over time as a result of decreases in DAGL functional expression (TG) and increases in 2AG degradation by MAGL and ABHD6 (Cortex, PAG). Moreover, it was shown that induction of facial allodynia confers a shift in 2AG signaling away from CB1R. Importantly, such experiments demonstrated that inhibition of MAGL and ABHD6 profoundly attenuated periorbital allodynia occurring after cortical KCl injection and indicated unique roles for MAGL and ABHD6 in reversal and prevention of facial sensitivity, respectively. As such, such experiments indicate that induction of headache pain results from enhanced degradation of 2AG by MAGL and ABHD6 that can be targeted pharmaceutically.

Accordingly, the present invention relates generally to compositions and methods for preventing, reducing the occurrence of or treating a headache in a subject in need thereof. In particular, the present invention relates to methods for enhancing 2-arachydonyl glycerol (2AG) tone and reducing prostaglandin activity in a subject for purposes of preventing, reducing the occurrence of or treating a headache (e.g., a migraine headache) in a subject.

In certain embodiments, the present invention provides a method of preventing, reducing the occurrence of or treating a headache in a mammal comprising administering to the mammal a pharmaceutical composition capable of enhancing 2AG tone in the mammal.

In certain embodiments, the present invention provides a method of preventing, reducing the occurrence of or treating a headache in a mammal comprising administering to the mammal a pharmaceutical composition capable of inhibiting prostaglandin activity in the mammal.

In certain embodiments, the present invention provides a method of preventing, reducing the occurrence of or treating a headache in a mammal comprising administering to the mammal a pharmaceutical composition capable of enhancing 2AG tone and inhibiting prostaglandin activity in the mammal.

Such methods are not limited to a particular type of mammal. In some embodiments, the mammal is a human being. In some embodiments, the mammal is a human being suffering from or at risk of suffering from a headache (e.g., a migraine headache).

Such methods are not limited to treating a particular type or kind of headache. In some embodiments, the headache is a non-migraine headache. In some embodiments, the headache is a migraine headache. In some embodiments, the migraine headache is a chronic migraine headache. In some embodiments, the headache is an episodic migraine headache.

Such methods are not limited to a particular type of pharmaceutical composition capable of enhancing 2AG tone and/or reducing prostaglandin activity in the mammal.

In some embodiments, the pharmaceutical composition capable of enhancing 2AG tone and/or reducing prostaglandin activity in the mammal comprises an agent capable of inhibiting MAGL expression and/or activity levels. In some embodiments, the agent capable of inhibiting MAGL expression and/or activity levels is MJN110 (e.g.,

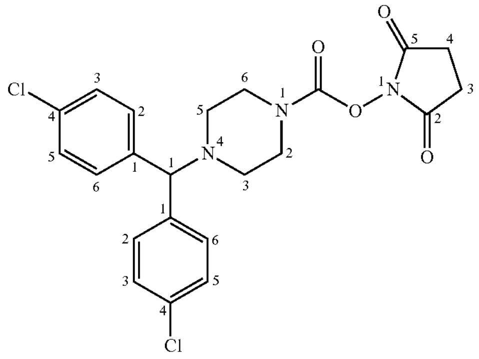 [SMILES: O=C(ON1C(=O)CCC1=O)N1CCN(C(c2ccc(Cl)cc2)c2ccc(Cl)cc2)CC1]

2,5-dioxopyrrolidin-1-yl 4-(bis(4-chlorophenyl)methyl) piperazine-1-carboxylate). In some embodiments, the agent capable of inhibiting MAGL expression and/or activity levels is structurally similar to MJN110. In some embodiments, the agent capable of inhibiting MAGL expression and/or activity levels is small molecule. In some embodiments, the agent capable of inhibiting MAGL expression and/or activity levels is peptide. In some embodiments, the agent capable of inhibiting MAGL expression and/or activity levels is an antibody.

In some embodiments, the pharmaceutical composition capable of enhancing 2AG tone and/or reducing prostaglandin activity in the mammal comprises an agent capable of inhibiting ABHD6 expression and/or activity levels. In some embodiments, the agent capable of inhibiting

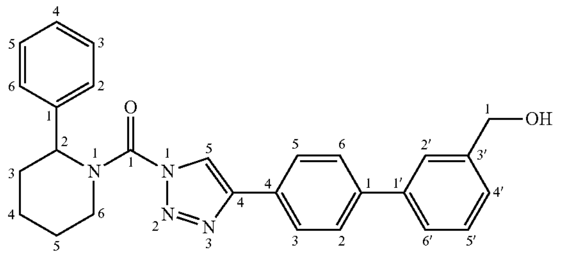

(4-(3'-(hydroxymethyl)-[1,1'-biphenyl]-4-yl)-1H-1,2,3-triazol-1-yl)(2-phenylpiperidin-1-yl) methanone). In some embodiments, the agent capable of inhibiting ABHD6 expression and/or activity levels is structurally similar to KT182. In some embodiments, the agent capable of inhibiting ABHD6 expression and/or activity levels is small molecule. In some embodiments, the agent capable of inhibiting ABHD6 expression and/or activity levels is peptide. In some embodiments, the agent capable of inhibiting ABHD6 expression and/or activity levels is an antibody.

In some embodiments, the pharmaceutical composition capable of enhancing 2AG tone and/or reducing prostaglandin activity in the mammal comprises an agent capable of inhibiting ABHD12 expression and/or activity levels. In some embodiments, the agent capable of inhibiting ABHD12 expression and/or activity levels is small molecule. In some embodiments, the agent capable of inhibiting ABHD12 expression and/or activity levels is peptide. In some embodiments, the agent capable of inhibiting ABHD12 expression and/or activity levels is an antibody.

In some embodiments, the pharmaceutical composition capable of enhancing 2AG tone and/or reducing prostaglandin activity in the mammal comprises an agent capable of enhancing DAGL expression and/or activity levels. In some embodiments, the agent capable of enhancing DAGL expression and/or activity levels is small molecule. In some embodiments, the agent capable of enhancing DAGL expression and/or activity levels is peptide. In some embodiments, the agent capable of enhancing DAGL expression and/or activity levels is an antibody.

In some embodiments, the pharmaceutical composition capable of enhancing 2AG tone and/or reducing prostaglandin activity in the mammal comprises one or more of the following agents: an agent capable of inhibiting MAGL activity and/or expression (e.g., MJN110), an agent inhibiting ABHD12 activity and/or expression, and an agent capable of enhancing DAGL activity and/or expression.

In some embodiments, the pharmaceutical composition capable of enhancing 2AG tone and/or reducing prostaglandin activity in the mammal comprises MJN110 and KT182.

In some embodiments, the methods further comprise co-administration of a pharmaceutical composition comprising a second agent (e.g., 5-HT1 agonists, triptans, ergot alkaloids, and non-steroidal anti-inflammatory drugs).

In certain embodiments, the present invention provides a method of enhancing 2AG tone and/or inhibiting prostaglandin activity in a mammal, comprising administering to the subject an agent capable of inhibiting MAGL expression and/or activity levels. In some embodiments, the agent capable of inhibiting MAGL expression and/or activity levels is MJN110.

In certain embodiments, the present invention provides a method of enhancing 2AG tone and/or inhibiting prostaglandin activity in a mammal, comprising administering to the subject an agent capable of inhibiting ABHD6 expression and/or activity levels. In some embodiments, the agent capable of inhibiting ABHD6 expression and/or activity levels is KT182.

In certain embodiments, the present invention provides a method of enhancing 2AG tone and/or inhibiting prostaglandin activity in a mammal, comprising administering to the subject an agent capable of inhibiting ABHD12 expression and/or activity levels.

In certain embodiments, the present invention provides a method of enhancing 2AG tone and/or inhibiting prostaglandin activity in a mammal, comprising administering to the subject an agent capable of enhancing DAGL expression and/or activity levels.

The methods and compositions of the present invention are useful in treating mammals. Such mammals include humans as well as non-human mammals. Non-human mammals include, for example, companion animals such as dogs and cats, agricultural animals such live stock including cows, horses and the like, and exotic animals, such as zoo animals.

Administration of such pharmaceutical compositions can be by any suitable route of administration including buccal, dental, endocervical, intramuscular, inhalation, intracranial, intralymphatic, intramuscular, intraocular, intraperitoneal, intrapleural, intrathecal, intratracheal, intrauterine, intravascular, intravenous, intravesical, intranasal, ophthalmic, oral, otic, biliary perfusion, cardiac perfusion, priodontal, rectal, spinal subcutaneous, sublingual, topical, intravaginal, transermal, ureteral, or urethral. Dosage forms can be aerosol including metered aerosol, chewable bar, capsule, capsule containing coated pellets, capsule containing delayed release pellets, capsule containing extended release pellets, concentrate, cream, augmented cream, suppository cream, disc, dressing, elixer, emulsion, enema, extended release fiber, extended release film, gas, gel, metered gel, granule, delayed release granule, effervescent granule, chewing gum, implant, inhalant, injectable, injectable lipid complex, injectable liposomes, insert, extended release insert, intrauterine device, jelly, liquid, extended release liquid, lotion, augmented lotion, shampoo lotion, oil, ointment, augmented ointment, paste, pastille, pellet, powder, extended release powder, metered powder, ring, shampoo, soap solution, solution for slush, solution/drops, concentrate solution, gel forming solution/drops, sponge, spray, metered spray, suppository, suspension, suspension/drops, extended release suspension, swab, syrup, tablet, chewable tablet, tablet containing coated particles, delayed release tablet, dispersible tablet, effervescent tablet, extended release tablet, orally disintegrating tablet, tampon, tape or troche/lozenge.

Intraocular administration can include administration by injection including intravitreal injection, by eyedrops and by trans-scleral delivery.

Administration can also be by inclusion in the diet of the mammal such as in a functional food for humans or companion animals.

It is also contemplated that certain formulations containing the compositions capable of enhancing AG tone and/or inhibiting prostaglandin levels are to be administered orally. Such formulations are preferably encapsulated and formulated with suitable carriers in solid dosage forms. Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, gelatin, syrup, methylcellulose, methyl- and propylhydroxy benzoates, talc, magnesium, stearate, water, mineral oil, and the like. The formulations can additionally include lubricating agents, wetting agents, emulsifying and suspending agents, preserving agents, sweetening agents or flavoring agents. The compositions may be formulated such as to provide rapid, sustained, or delayed release of the active ingredients after administration to the patient by employing procedures well known in the art. The formulations can also contain substances that diminish proteolytic degradation and promote absorption such as, for example, surface-active agents.

The specific dose can be calculated according to the approximate body weight or body surface area of the patient or the volume of body space to be occupied. The dose will also depend upon the particular route of administration selected. Further refinement of the calculations necessary to determine the appropriate dosage for treatment is routinely made by those of ordinary skill in the art. Such calculations can be made without undue experimentation by one skilled in the art in light of the activity in assay preparations such as has been described elsewhere for certain compounds (see for example, Howitz et al., Nature 425:191-196, 2003 and supplementary information that accompanies the paper). Exact dosages can be determined in conjunction with standard dose-response studies. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration.

The present invention also provides kits comprising compositions capable of enhancing AG tone and/or inhibiting prostaglandin levels and instructions for administering the pharmaceutical composition to an animal (e.g., a human patient suffering from a headache (e.g., a migraine headache)). The kits may optionally contain other therapeutic agents.

EXPERIMENTAL

The following examples are provided to demonstrate and further illustrate certain preferred embodiments of the present invention and are not to be construed as limiting the scope thereof.

Example I

Experiments conducted during the course of developing embodiments for the present invention tackled this major gap in migraine pathology by elucidating the role of endocannabinoids in migraine, using an integrated approach of analytical chemistry, molecular biology, systems neuropharmacology and functional expression analyses.

Monoacylglycerol lipase (MAGL), ABHD6 and ABHD12 are key enzymes in the hydrolysis of the endocannabinoid, 2-arachidonoylglycerol (2-AG), whereas DAGL is the major enzyme generating 2-AG in the central nervous system. Such experiments indicated that overactivity of MAGL and loss of DAGL expression in regionally distinct areas of the trigeminal pain axis with temporal dynamics following cortical injection of KCl. Experiments were conducted with the postulation that pathogenic remodeling of the 2AG endocannabinoid signaling system plays a critical role in the generation of headache pain that can be targeted therapeutically. It was shown that increasing eCB tone by targeting either MAGL, ABHD6, and/or ABHD12 as an effective strategy for headache therapy (e.g., migraine therapy). Such experiments resulted in the discovery that endogenous 2AG levels in four discrete nuclei associated with headache (e.g., cortex, periaqueductal grey-PAG, trigeminal nucleus caudalis-Vc, and the trigeminal ganglia-TG) are regionally regulated over time as a result of decreases in DAGL functional expression (TG) and increases in 2AG degradation by MAGL and ABHD6 (Cortex, PAG). Moreover, it was shown that induction of facial allodynia confers a shift in 2AG signaling away from CB1R. Importantly, such experiments demonstrated that inhibition of MAGL and ABHD6 profoundly attenuated periorbital allodynia occurring after cortical KCl injection and indicated unique roles for MAGL and ABHD6 in reversal and prevention of facial sensitivity, respectively. As such, such experiments indicate that induction of headache pain results from enhanced degradation of 2AG by MAGL and ABHD6 that can be targeted pharmaceutically.

FIG. 1 depicts a summary of specific aims of the experiments described in Example I.

As shown in FIG. 2, experiments were conducted demonstrating that cortical KCl, but not dural KCl, induces periorbital allodynia in female rats and activates cFOS.

As shown in FIG. 3, experiments were conducted demonstrating that 2AG, but not AEA levels, were altered after cortical KCl in region-specific manner.

As shown in FIG. 4, experiments were conducted demonstrating that MAGL expression in cortex and TG 90 minutes after cortical aCSF or KCl.

As shown in FIG. 5, experiments were conducted demonstrating expression/activity of ABHD6 and MAGL in naïve rat Cortex, and enzyme activity of both ABHD6 and MAGL in Cortex were statistically unaffected by cortical aCSF or KCl.

As shown in FIG. 6, experiments were conducted demonstrating CB1R protein expression is reduced 90 min after cortical KCl in cortex, PAG, and TG but not following aCSF as compared to naïve one-way ANOVA $^*p<0.05$.

As shown in FIG. 7, experiments were conducted demonstrating that A) protein levels of CB2R were assessed 90 min postaCSF/KCl injection and no significant changes as compared to naïve were observed; and mRNA expression of the CB2 gene CNR2 was evaluated. CNR2 mRNA was shown to be increased 180 min after cortical KCl in Cortex (B) but not in the PAG (C) or TG (D) suggesting dynamic changes in the ECS in this model.

As shown in FIG. 8, experiments were conducted demonstrating that MAGL inhibition alleviates cortical KCl induced periorbital allodynia in female rats. Injection of MJN110 (10 mg/kg. IP) before or after cortical KCl (IM, 0.5 μL) significantly (A) prevents and (B) reverses periorbital allodynia. Data are expressed mean±SEM (n=8-12), two-way RMANOVA Bonferroni, $^*p<0.051$ $^{}p<0.01$: $^{**}p<0.0001$.

As shown in FIG. 9, experiments were conducted demonstrating that ABHD6 inhibition alleviates cortical KCl induced periorbital allodynia in female rats. Injection of KT182 (2 mg/kg, IP) before or after cortical KCl (IM, 0.5 μL) significantly prevents (A) and reverses (B) periorbital allodynia. Data are expressed mean±SEM (n=8-12), two-way RMANOVA Bonferroni, $^*p<0.05$: $^{}p<0.01$: $^{*}p<0.001$.

As shown in FIG. 10, experiments were conducted demonstrating that dual MAGL/ABHD6 inhibition alleviates cortical KCl induced periorbital allodynia in female rats. Co-injection of MJN (10 mg/kg IP) with KT182 (2 mg/kg, IP) before or after cortical KCl (IM, 0.5 μL) significantly prevents (A) and reverses (B) facial allodynia. Data are expressed mean+SEM (n=7-14), two-way RMANOVA, Bonferroni, *p<0.05: p<0.01: **p<0.0001.

As shown in FIG. 11, experiments were conducted demonstrating that AUCs for vehicle, MJN110 (10 mg/kg IP), KT182 (2 mg/kg, IP), and co-injected MJN110 & KT182 before (A) or after (B) cortical KCl (IM, 0.5 μL) Data are expressed mean±SEM (n=7-14), one-way ANOVA Bonferroni, *p<0.05, **p<0.01.

As shown in FIG. 12, experiments were conducted demonstrating that a schematic of the Cas9/sgRNA system targeting the first exon of MGII (monoacylglycerol lipase gene).

As shown in FIG. 13, experiments were conducted demonstrating that MAGL inhibition and cannabinoid receptor selectivity. Injection of CB1R antagonist, rimonabant (1 mg/kg, IP) prior to KCl shifted onset of MJN110 (10 mg/kg, IP) by 30 min. CB2R antagonist, SR144528 (1 mg/kg, IP), injected prior to KCl blocked the anti-allodynic effect of MJN110. Data are expressed mean #SEM (n=9), one- and two-way ANOVA, *p<0.05, *p<0.001, **p<0.0001.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

The following references are incorporated herein in their entireties:

1. Burch, R. C., et al., *The prevalence and burden of migraine and severe headache in the United States: updated statistics from government health surveillance studies*. Headache, 2015. 55 (1): p. 21-34.
2. *Global, regional, and national burden of migraine and tension-type headache*. 1990-2016*: a systematic analysis for the Global Burden of Disease Study* 2016. Lancet Neurol, 2018. 17 (11): p. 954-976.
3. Smitherman, T. A., et al., *The prevalence, impact, and treatment of migraine and severe headache in the United States: a review of statistics from national surveillance studies*. Headache, 2013. 53 (3): p. 427-36.
4. Silberstein, S. D., *Headache and female hormones: what you need to know*. Curr Opin Neurol, 2001. 14 (3): p. 323-33.
5. Eikermann-Haerter, K., et al., *Genetic and hormonal factors modulate spreading depression and transient hemiparesis in mouse models of familial hemiplegic migraine type* 1. J Clin Invest, 2009. 119 (1): p. 99-109.
6. Fioravanti, B., et al., *Evaluation of cutaneous allodynia following induction of cortical spreading depression in freely moving rats*. Cephalalgia, 2011. 31 (10): p. 1090-100.
7. Gault, L. M., et al., *Changes in energy metabolites, cGMP and intracellular pH during cortical spreading depression*. Brain Res, 1994. 641 (1): p. 176-80.
8. Pusic, A. D., et al., *Spreading depression transiently disrupts myelin via interferon-gamma signaling*. Experimental neurology, 2015. 264: p. 43-54.
9. Cozzolino, O., et al., *Understanding Spreading Depression from Headache to Sudden Unexpected Death*. Frontiers in Neurology, 2018. 9 (19).
10. Hartings, J. A., et al., *The continuum of spreading depolarizations in acute cortical lesion development: Examining Leao's legacy*. J Cereb Blood Flow Metab, 2017. 37 (5): p. 1571-1594.
11. Lauritzen, M., et al., *Clinical relevance of cortical spreading depression in neurological disorders: migraine, malignant stroke, subarachnoid and intracranial hemorrhage, and traumatic brain injury*. J Cereb Blood Flow Metab, 2011. 31 (1): p. 17-35.
12. Andrew, R. D., Y. T. Hsieh, and C. D. Brisson, *Spreading depolarization triggered by elevated potassium is weak or absent in the rodent lower brain*. J Cereb Blood Flow Metab, 2017. 37 (5): p. 1735-1747.
13. Csiba, L., W. Paschen, and G. Mies, *Regional changes in tissue pH and glucose content during cortical spreading depression in rat brain*. Brain Res, 1985. 336 (1): p. 167-70.
14. Kurauchi, Y., et al., *Propranolol prevents cerebral blood flow changes and pain-related behaviors in migraine model mice*. Biochem Biophys Res Commun, 2019. 508 (2): p. 445-450.
15. Moskowitz, M. A., *The neurobiology of vascular head pain*. Ann Neurol, 1984. 16 (2): p. 157-68.
16. Sun, X., et al., *Simultaneous monitoring of intracellular pH changes and hemodynamic response during cortical spreading depression by fluorescence-corrected multimodal optical imaging*. Neuroimage, 2011. 57 (3): p. 873-84.
17. Harriott, A. M., et al., *Spreading depression as a preclinical model of migraine*. J Headache Pain, 2019. 20 (1): p. 45.
18. Hansen, A. J. and T. Zeuthen, *Extracellular ion concentrations during spreading depression and ischemia in the rat brain cortex*. Acta Physiol Scand, 1981. 113 (4): p. 437-45.
19. Jacobs, B. and G. Dussor, *Neurovascular contributions to migraine: Moving beyond vasodilation*. Neuroscience, 2016. 338: p. 130-144.
20. Busija, D. W., et al., *Mechanisms involved in the cerebrovascular dilator effects of cortical spreading depression*. Prog Neurobiol, 2008. 86 (4): p. 379-95.
21. Blicher, J. U., et al., *Perfusion and pH MRI in familial hemiplegic migraine with prolonged aura*. Cephalalgia, 2015.
22. Cernuda-Morollon, E., et al., *Interictal increase of CGRP levels in peripheral blood as a biomarker for chronic migraine*. Neurology, 2013. 81 (14): p. 1191-6.
23. Durham, P. and S. Papapetropoulos, *Biomarkers associated with migraine and their potential role in migraine management*. Headache, 2013. 53 (8): p. 1262-77.
24. Boes, T. and D. Levy, *Influence of sex, estrous cycle, and estrogen on intracranial dural mast cells*. Cephalalgia, 2012. 32 (12): p. 924-31.
25. Edelmayer, R. M., M. H. Ossipov, and F. Porreca, *An experimental model of headache-related pain*. Methods Mol Biol, 2012. 851: p. 109-20.
26. Lundblad, C., et al., *Experimental inflammation following dural application of complete Freund's adjuvant or inflammatory soup does not alter brain and trigeminal microvascular passage*. J Headache Pain, 2015. 16 (1): p. 91.
27. Yan, J., et al., *pH-evoked dural afferent signaling is mediated by ASIC*3 *and is sensitized by mast cell mediators*. Headache, 2013. 53 (8): p. 1250-61.

28. Hadjikhani, N., et al., *Mechanisms of migraine aura revealed by functional MRI in human visual cortex*. Proc Natl Acad Sci USA, 2001. 98 (8): p. 4687-92.
29. Edelmayer, R. M., et al., *Activation of TRPAI on dural afferents: a potential mechanism of headache pain*. Pain, 2012. 153 (9): p. 1949-58.
30. Edelmayer, R. M., et al., *Medullary pain facilitating neurons mediate allodynia in headache-related pain*. Ann Neurol, 2009. 65 (2): p. 184-93.
31. *Marshall, A. C., et al., Evidence for an angiotensin-*(1-7) *neuropeptidase expressed in the brain medulla and CSF of sheep*. J Neurochem, 2014. 130 (2): p. 313-23.
32. Stucky, N. L., et al., *Sex differences in behavior and expression of CGRP-related genes in a rodent model of chronic migraine*. Headache, 2011. 51 (5): p. 674-92.
33. Kandasamy, R., A. T. Lee, and M. M. Morgan, *Depression of home cage wheel running: a reliable and clinically relevant method to assess migraine pain in rats*. J Headache Pain, 2017. 18 (1): p. 5.
34. Khanna, R., et al., *Development and Characterization of An Injury-free Model of Functional Pain in Rats by Exposure to Red Light*. J Pain, 2019.
35. Reggio, P. H., *Endocannabinoid binding to the cannabinoid receptors: what is known and what remains unknown*. Current medicinal chemistry, 2010. 17 (14): p. 1468-1486.
36. Jia, Z., et al., *Disrupted functional connectivity between the periaqueductal gray and other brain regions in a rat model of recurrent headache*. Sci Rep, 2017. 7 (1): p. 3960.
37. Chanda, D., D. Neumann, and J. F. C. Glatz, *The endocannabinoid system: Overview of an emerging multifaceted therapeutic target*. Prostaglandins Leukot Essent Fatty Acids, 2019. 140: p. 51-56.
38. Nomura, D. K., et al., *Endocannabinoid hydrolysis generates brain prostaglandins that promote neuroinflammation*. Science, 2011. 334 (6057): p. 809-13.
39. Yirmiya, R. and I. Goshen, *Immune modulation of learning, memory, neural plasticity and neurogenesis*. Brain Behav Immun, 2011. 25 (2): p. 181-213.
40. Sundrum, T. and C. S. Walker, *Pituitary adenylate cyclase-activating polypeptide receptors in the trigeminovascular system: implications for migraine*. Br J Pharmacol, 2018. 175 (21): p. 4109-4120.
41. Formicola, D., et al., *Common variants in the regulative regions of GRIAI and GRIA*3 *receptor genes are associated with migraine susceptibility*. BMC Med Genet, 2010. 11: p. 103.
42. Hollenstein, K., et al., *Insights into the structure of class B GPCRs*. Trends Pharmacol Sci, 2014. 35 (1): p. 12-22.
43. Stone, L. S. and D. C. Molliver, *In search of analgesia: emerging roles of GPCRs in pain*. Mol Interv, 2009. 9 (5): p. 234-51.
44. Soethoudt, M., et al., *Cannabinoid CB*2 *receptor ligand profiling reveals biased signalling and off-target activity*. Nature Communications, 2017. 8 (1): p. 13958.
45. Harlan, B. A., et al., *Opposing actions of CRF-RI and CB*1 *receptors on VTA-GABAergic plasticity following chronic exposure to ethanol*. Neuropsychopharmacology, 2018. 43 (10): p. 2064-2074.
46. Hoffman, A. F., A. C. Riegel, and C. R. Lupica, *Functional localization of cannabinoid receptors and endogenous cannabinoid production in distinct neuron populations of the hippocampus*. Eur J Neurosci, 2003. 18 (3): p. 524-34.
47. Sanchez-Blazquez, P., M. Rodriguez-Munoz, and J. Garzon, *The cannabinoid receptor* 1 *associates with NMDA receptors to produce glutamatergic hypofunction: implications in psychosis and schizophrenia*. Front Pharmacol, 2014. 4: p. 169.
48. Murataeva, N., A. Straiker, and K. Mackie, *Parsing the players:* 2-*arachidonoylglycerol synthesis and degradation in the CNS*. British journal of pharmacology, 2014. 171 (6): p. 1379-1391.
49. Gong, J. P., et al., *Cannabinoid CB*2 *receptors: immunohistochemical localization in rat brain*. Brain Res, 2006. 1071 (1): p. 10-23.
50. Navarrete, F., et al., *Role of CB*2 *cannabinoid receptors in the rewarding, reinforcing, and physical effects of nicotine*. Neuropsychopharmacology, 2013. 38 (12): p. 2515-24.
51. Ortega-Alvaro, A., et al., *Role of cannabinoid CB*2 *receptor in the reinforcing actions of ethanol*. Addict Biol, 2015. 20 (1): p. 43-55.
52. Xi, Z. X., et al., *Brain cannabinoid CB* (2) *receptors modulate cocaine's actions in mice*. Nat Neurosci, 2011. 14 (9): p. 1160-6.
53. Zhang, H. Y., et al., *Cannabinoid CB*2 *receptors modulate midbrain dopamine neuronal activity and dopaminerelated behavior in mice*. Proc Natl Acad Sci USA, 2014. 111 (46): p. E5007-15.
54. Zhang J., H. C., Vu H. K., Groblewski T., Ahmad S., and O.D. D., *Induction of CB*2 *receptor expression in the ratspinal cord of neuropathic but not inflammatory chronicpain models*. European Journal of Neuroscience, 2003. 17 p. 2750-2754.
55. Grenald, S. A., et al., S*ynergistic attenuation of chronic pain using mu opioid and cannabinoid receptor* 2 *agonists*. Neuropharmacology, 2017. 116: p. 59-70.
56. Ignatowska-Jankowska, B. M., et al., *The cannabinoid CB*2 *receptor is necessary for nicotine-conditioned place preference, but not other behavioral effects of nicotine in mice*. Psychopharmacology (Berl), 2013. 229 (4): p. 591-601.
57. Cohen, C., E. Kodas, and G. Griebel, *CB*1 *receptor antagonists for the treatment of nicotine addiction*. Pharmacol Biochem Behav, 2005. 81 (2): p. 387-95.
58. Cossu, G., et al., *Cannabinoid CB*1 *receptor knockout mice fail to self-administer morphine but not other drugs of abuse*. Behav Brain Res, 2001. 118 (1): p. 61-5.
59. Covey, D. P., J. M. Wenzel, and J. F. Cheer, *Cannabinoid modulation of drug reward and the implications of marijuana legalization*. Brain Res, 2014.
60. Le Foll, B. and S. R. Goldberg, *Rimonabant, a CB*1 *antagonist, blocks nicotine-conditioned place preferences*. Neuroreport, 2004. 15 (13): p. 2139-43.
61. Burston, J. J. and S. G. Woodhams, *Endocannabinoid system and pain: an introduction*. Proc Nutr Soc, 2014. 73 (1): p. 106-17.
62. Sailler, S., et al., *Regulation of circulating endocannabinoids associated with cancer and metastases in mice and humans*. Oncoscience, 2014. 1 (4): p. 272-82.
63. Abidi, A. H., et al., *Anti-inflammatory activity of cannabinoid receptor* 2 *ligands in primary hPDL fibroblasts*. Arch Oral Biol, 2018. 87: p. 79-85.
64. Luk, T., et al., *Identification of a potent and highly efficacious, yet slowly desensitizing CB*1 *cannabinoid receptor agonist*. Br J Pharmacol, 2004. 142 (3): p. 495-500.
65. Kind, L. and P. Kursula, *Structural properties and role of the endocannabinoid lipases ABHD*6 *and ABHD*12 *in lipid signalling and disease*. Amino Acids, 2019. 51 (2): p. 151-174.

66. Dhopeshwarkar, A. and K. Mackie, *Functional Selectivity of CB2 Cannabinoid Receptor Ligands at a Canonical and Noncanonical Pathway*. J Pharmacol Exp Ther, 2016. 358 (2): p. 342-51.
67. Cao, J. K., J. Kaplan, and N. Stella, *ABHD6: Its Place in Endocannabinoid Signaling and Beyond*. Trends Pharmacol Sci, 2019. 40 (4): p. 267-277.
68. Marrs, W. R., et al., *The serine hydrolase ABHD6 controls the accumulation and efficacy of 2-AG at cannabinoid receptors*. Nat Neurosci, 2010. 13 (8): p. 951-7.
69. Anderson, W. B., et al., *Actions of the dual FAAH MAGL inhibitor JZL195 in a murine inflammatory pain model*. Neuropharmacology, 2014. 81: p. 224-30.
70. Davis, M. P., *Cannabinoids in pain management: CB1. CB2 and non-classic receptor ligands*. Expert Opin Investig Drugs, 2014. 23 (8): p. 1123-40.
71. Ibrahim, M. M., et al., *CB2 cannabinoid receptor mediation of antinociception*. Pain, 2006. 122 (1-2): p. 36-42.
72. Lozano-Ondoua, A. N., et al., *Disease modification of breast cancer-induced bone remodeling by cannabinoid 2 receptor agonists*. J Bone Miner Res, 2013. 28 (1): p. 92-107.
73. Lozano-Ondoua, A. N., et al., *A cannabinoid 2 receptor agonist attenuates bone cancer-induced pain and bone loss*. Life Sci, 2010. 86 (17-18): p. 646-53.
74. Pascual, D., et al., *A cannabinoid agonist. WIN 55.212-2, reduces neuropathic nociception induced by paclitaxel in rats*. Pain, 2005. 118 (1-2): p. 23-34.
75. Sarchielli, P., et al., *Endocannabinoids in Chronic Migraine: CSF Findings Suggest a System Failure*. Neuropsychopharmacology, 2007. 32 (6): p. 1384-1390.
76. Greco, R., et al., *Endocannabinoid System and Migraine Pain: An Update*. Front Neurosci, 2018. 12. p. 172.
77. Russo, E. B. *Clinical endocannabinoid deficiency (CECD): can this concept explain therapeutic benefits of cannabis in migraine, fibromyalgia, irritable bowel syndrome and other treatment-resistant conditions?* Neuro Endocrinol Lett, 2008. 29 (2): p. 192-200.
78. G*lobal, regional, and national burden of neurological disorders. 1990-2016: a systematic analysis for the Global Burden of Disease Study 2016*. Lancet Neurol, 2019. 18 (5): p. 459-480.
79. Borsook, D., et al., *Sex and the migraine brain*. Neurobiol Dis, 2014. 68: p. 200-14.
80. Buse, D. C., et al., *Sex differences in the prevalence, symptoms, and associated features of migraine, probable migraine and other severe headache: results of the American Migraine Prevalence and Prevention (AMPP) Study*. Headache, 2013. 53 (8): p. 1278-99.
81. Karli, N., et al., *Impact of sex hormonal changes on tension-type headache and migraine: a cross-sectional population-based survey in 2.600 women*. J Headache Pain, 2012. 13 (7): p. 557-65.
82. Greco, R., et al., *The endocannabinoid system and migraine*. Exp Neurol 2010. 224 (1): p. 85-91.
83. Cupini, L. M., et al., *Biochemical changes in endocannabinoid system are expressed in platelets of female but not male migraineurs*. Cephalalgia, 2006. 26 (3): p. 277-81.
84. Baron, E. P., *Medicinal Properties of Cannabinoids. Terpenes, and Flavonoids in Cannabis. and Benefits in Migraine. Headache, and Pain: An Update on Current Evidence and Cannabis Science*. Headache, 2018. 58 (7): p. 1139-1186.
85. Baron, E. P., et al., *Patterns of medicinal cannabis use*, strain *analysis*, and *substitution effect among patients with migraine, headache, arthritis*, and *chronic pain in a medicinal cannabis cohort*. J Headache Pain, 2018. 19 (1): p. 37.
86. Forderreuther, S., [*Cannabis in headache treatment*]. MMW Fortschr Med, 2018. 160 (Suppl 1): p. 70-71.
87. Lochte, B. C., et al., *The Use of Cannabis for Headache Disorders*. Cannabis Cannabinoid Res, 2017. 2 (1): p. 61-71.
88. Banerjee, S. and S. McCormack, *CADTH Rapid Response Reports, in Medical Cannabis for the Treatment of Chronic Pain: A Review of Clinical Effectiveness and Guidelines*. 2019, Canadian Agency for Drugs and Technologies in Health. Copyright (c) 2019 Canadian Agency for Drugs and Technologies in Health.: Ottawa (ON).
89. Cuttler, C., et al., *Short-and Long-Term Effects of Cannabis on Headache and Migraine*. J Pain, 2019.
90. Adorjan, K., et al., *Epileptic Spikes in EEG and Migraine Attacks in the Course of Cannabis Withdrawal: A Case Report*. Clin EEG Neurosci, 2020. 51 (1): p. 45-50.
91. Kandasamy, R., et al., *Anti-migraine effect of* (9)-*tetrahydrocannabinol in the female rat*. Eur J Pharmacol, 2018. 818: p. 271-277.
92. Kandasamy, R., et al., M*edication overuse headache following repeated morphine, but not [INCREMENT] 9-tetrahydrocannabinol administration in the female rat*. Behav Pharmacol, 2018. 29 (5): p. 469-472.
93. Kopruszinski, C. M., et al., *Cannabinoids induce latent sensitization in a preclinical model of medication overuse headache*. Cephalalgia, 2019: p. 333102419865252.
94. Leimuranta, P., et al., *Emerging role of (endo) cannabinoids in migraine*. Front Pharmacol 2018. 9:420.
95. Nozaki, C., et al., *Inhibition of FAAH reduces nitroglycerine-induced migraine-like pain and trigeminal neuronal hyperactivity in mice*. Eur Neuropsychophramacol, 2015. 25 (8): p. 1388-96.
96. Greco, R., et al., *Effects of peripheral FAAH blockade on NTG-induced hyperalgesia-evaluation of URB937 in an animal model of migraine*. Cephalgia, 2015. 35 (12): p. 1065-76.
97. Rimplejeet, K., et al., *What failed BIA 10-2474 Phase I clinical trial? Global speculations and recommendations for future Phase I trials*. J Pharmacol Pharmacother, 2016. 7 (3): p. 120-6.
98. Greco, R., et al., *Inhibition of monoacylglycerol lipase: Another signalling pathway for potential therapeutic targets in migraine?* Cephalalgia, 2018. 38 (6): p. 1138-1147.
99. Greco, R., et al., *FAAH inhibition as a preventive treatment for migraine: A pre-clinical study*. Neurobiol Dis, 2019. 134: p. 104624.
100. Tuo, W., et al., *Therapeutic potential of fatty acid amide hydrolase, monoacylglycerol lipase, and Nacylethanolamine acid amidase inhibitors*. J Med Chem, 2017. 60 (1): p. 4-46.
101. Adamson Barnes, N. S., et al., *Actions of the dual FAAH MAGL inhibitor JZL195 in a murine neuropathic pain model*. Br J Pharmacol, 2016. 173 (1): p. 77-87.
102. Chang, J. W., et al., *Highly selective inhibitors of monoacylglycerol lipase bearing a reactive group that is bioisosteric with endocannabinoid substrates*. Chem Biol, 2012. 19 (5): p. 579-88.
103. Kinsey, S. G., et al., *Fatty acid amide hydrolase and monoacylglycerol lipase inhibitors produce anti-allodynic effects in mice through distinct cannabinoid receptor mechanisms*. J Pain, 2010. 11 (12): p. 1420-8.
104. Sakin, Y. S., et al., *The effect of FAAH. MAGL, and Dual FAAH MAGL inhibition on inflammatory and col-*

*orectal distension-induced visceral pain models in Rodents*. Neurogastroenterol Motil, 2015. 27 (7): p. 936-44.

105. Zubrzycki, M., et al., *Effects of centrally administered endocannabinoids and opioids on orofacial pain perception in rats*. Br J Pharmacol, 2017. 174 (21): p. 3780-3789.

106. Lau, B. K., et al., *Endocannabinoid modulation by FAAH and monoacylglycerol lipase within the analgesic circuitry of the periaqueductal grey*. Br J Pharmacol, 2014. 171 (23): p. 5225-36.

107. Owens, R. A., et al., *Discriminative Stimulus Properties of the Endocannabinoid Catabolic Enzyme Inhibitor SA*-57 *in Mice*. J Pharmacol Exp Ther, 2016. 358 (2): p. 306-14.

108. Seillier, A., D. *Dominguez Aguilar, and A. Giuffrida, The dual FAAH MAGL inhibitor JZL*195 *has enhanced effects on endocannabinoid transmission and motor behavior in rats as compared to those of the MAGL inhibitor JZL*184. Pharmacol Biochem Behav, 2014. 124: p. 153-9.

109. Bera, S. C., et al., *A comparative study of psychiatric comorbidity, quality of life and disability in patients with migraine and tension type headache*. Neurol India, 2014. 62 (5): p. 516-20.

110. Dreier, Jens P. and C. Reiffurth, *The Stroke-Migraine Depolarization Continuum*. Neuron, 2015. 86 (4): p. 902-922.

111. Dai, Y. J., et al., *Potential Beneficial Effects of Probiotics on Human Migraine Headache: A Literature Review*. Pain Physician, 2017. 20 (2): p. E251-e255.

112. Evans, R. W., et al., *The FDA alert on serotonin syndrome with use of triptans combined with selective serotonin reuptake inhibitors or selective serotonin-norepinephrine reuptake inhibitors: American Headache Society position paper*. Headache, 2010. 50 (6): p. 1089-99.

113. Louter, M. A., et al., *Cutaneous allodynia as a predictor of migraine chronification*. Brain, 2013. 136 (11): p. 3489-3496.

114. Smith, S. C. and M. S. Wagner, *Clinical endocannabinoid deficiency* (*CECD*) *revisited: can this concept explain the therapeutic benefits of cannabis in migraine, fibromyalgia, irritable bowel syndrome and other treatment-resistant conditions*? Neuro Endocrinol Lett, 2014. 35 (3): p. 198-201.

115. Guindon, J., et al., *The endocannabinoid system and pain*. CNS Neurol Disord Drug Targets, 2009. 8 (6): 403-21.

116. Huang, W. J., et al., *Endocannabinoid system: Role in depression, reward and pain control*. Mol Med Rep, 2016. 14 (4): 2899-903.

117. Kendall, D. A,. et al., *Cannabinoid Receptors in the Central Nervous System: Their Signaling and Roles in Disease*. Front Cell Neurosci, 2017. 10:294.

118. Cottier, K. E., et al., Loss of Blood-Brain Barrier Integrity in a KCl-Induced Model of Episodic Headache Enhances CNS Drug Delivery. eNeuro, 2018. 5 (4).

119. Menyhart, A., et al., *Large-conductance Ca*(2+)*-activated potassium channels are potently involved in the inverse neurovascular response to spreading depolarization*. Neurobiol Dis, 2018. 119: p. 41-52.

120. Wang, Y., et al., *Induction of calcitonin gene-related peptide expression in rats by cortical spreading depression*. Cephalalgia, 2019. 39 (3): p. 333-341.

121. Liktor-Busa, E., et al., *Functional NHEI expression is critical to blood brain barrier integrity and sumatriptan blood to brain uptake*. bioRxiv, 2019: p. 2019.12.20.884247.

122. Mathew, N. T., Pathophysiology of chronic migraine and mode of action of preventive medications. Headache, 2011. 51 Suppl 2: p. 84-92.

123. Schwedt, T. J., et al., *Allodynia and descending pain modulation in migraine: a resting state functional connectivity analysis*. Pain Med, 2014. 15 (1): p. 154-65.

124. Tietjen, G. E., et al., *Allodynia in migraine: association with comorbid pain conditions*. Headache, 2009. 49 (9): p. 1333-44.

125. Charles, A. and K. Brennan, *Cortical spreading depression-new insights and persistent questions*. Cephalalgia, 2009. 29 (10): p. 1115-24.

126. Eising, E., et al., *Cortical Spreading Depression Causes Unique Dysregulation of Inflammatory Pathways in a Transgenic Mouse Model of Migraine*. Mol Neurobiol, 2017. 54 (4): p. 2986-2996.

127. Ayata, C., *Pearls and pitfalls in experimental models of spreading depression*. Cephalalgia, 2013. 33 (8): p. 604-13.

128. Sandweiss, A. J,. et al,. *Genetic and pharmacological antagonism of NKI receptor prevents opiate abuse potential*. Mol Psychiatry, 2017. 23 (8): p. 1745-55.

129. Ibrahim, M. M., et al., *Long-lasting antinociceptive effects of green light in acute and chronic pain in rats*. Pain, 2017. 158 (2): p. 347-60.

130. Hegarty, D. M., et al., *Capsaicin-responsive corneal afferents do not contain TRPV*1 *at their central terminals in trigeminal nucleus caudalis in rats*. J Chem Neuroanat, 2014. 61-62: p. 1-12.

131. Fried, N. T., et al., *Region-specific disruption of the blood-brain barrier following repeated inflammatory dural stimulation in a rat model of chronic trigeminal allodynia*. Cephalalgia, 2018. 38 (4): p. 674-689.

132. Avona, A., et al., *Dural Calcitonin Gene-Related Peptide Produces Female-Specific Responses in Rodent Migraine Models*. J Neurosci, 2019. 39 (22): p. 4323-4331.

133. Tassorelli, C., et al., *Nitroglycerin induces hyperalgesia in rats—a time-course study*. Eur J Pharmacol, 2003. 464 (2-3): p. 159-62.

134. Pardutz, A., et al., *Nitroglycerin-induced nNOS increase in rat trigeminal nucleus caudalis is inhibited by systemic administration of lysine acetylsalicylate but not of sumatriptan*. Cephalalgia, 2004. 24 (6): p. 439-45.

135. De Felice, M., et al., *Capturing the aversive state of cephalic pain preclinically*. Ann Neurol, 2013. 74 (2): p. 257-65.

136. Nation, K. M., et al., *Sustained exposure to acute migraine medications combined with repeated noxious stimulation dysregulates descending pain modulatory circuits: Relevance to medication overuse headache*. Cephalalgia, 2019. 39 (5): p. 617-625.

137. Gibbs, R. A., et al., *Genome sequence of the Brown Norway rat yields insights into mammalian evolution*. Nature, 2004. 428 (6982): p. 493-521.

138. Clayton, J. A., et al., *Policy: NIH to balance sex in cell and animal studies*. Nature, 2014. 509 (7500): p. 282-3.

139. Andrews, N. A., et al., *Ensuring transparency and minimization of methodologic bias in preclinical pain research: Precise considerations*. Pain, 2016. 157 (4): p. 901-9.

140. Chen, Z., et al., *Disrupted functional connectivity of periaqueductal gray subregions in episodic migraine*. J Headache Pain, 2017. 18 (1): p. 36.

141. Buczynski, M. W., et al., *Quantification of brain endocannabinoid levels: methods, interpretations and pitfalls*. Br J Pharmacol, 2010. 160 (3): p. 423-42.

142. Zoerner, A. A., et al., *Quantification of endocannabinoids in biological systems by chromatography and mass spectrometry: A comprehensive review from analytical and biological perspective*. Biochim Biophys Acta, 2011. 1811 (11): p. 706-23.

143. Greco, R., et al., *Alterations of the endocannabinoid system in an animal model of migraine: evaluation in cerebral areas of rat*. Cephalgia, 2010. 30 (3): p. 296-302.

144. Gentile, A., et al., *Interaction between interleukin-1β and type-1 cannabinoid receptor is involved in anxiety-like behavior in experimental autoimmune encephalomyelitis*. J Neuroinflammation, 2016. 13 (1): p. 231.

145. Daigle, T. L., et al., *Regulation of CB1 cannabinoid receptor internalization by a promiscuous phosphorylationdependent mechanism*. J Neurochem, 2008. 106 (1): p. 70-82.

146. Kingsley, P. J. and L. J. Marnett, *Analysis of endocannabinoids, their congeners and COX-2 metabolites*. J Chromatogr B Analyt Technol Biomed Life Sci, 2009. 877 (26): p. 2746-54.

147. Kingsley, P. J., et al., *Aspects of Prostaglandin Glycerol Ester Biology*. Adv Exp Med Biol, 2019. 1161: p. 77-88.

148. Kudalkar, S. N., P. J. Kingsley, and L. J. Marnett, *Assay of Endocannabinoid Oxidation by Cyclooxygenase-2*. Methods Mol Biol, 2016. 1412: p. 205-15.

149. Morgan, A. J., et al., *Detection of Cyclooxygenase-2-Derived Oxygenation Products of the Endogenous Cannabinoid 2-Arachidonoylglycerol in Mouse Brain*. ACS Chem Neurosci, 2018. 9 (7): p. 1552-1559.

150. Blancaflor, E. B., et al., *N-Acylethanolamines: lipid metabolites with functions in plant growth and development*. Plant J, 2014. 79 (4): p. 568-83.

151. Keereetaweep, J., et al., *Lipoxygenase-derived 9-hydro (pero) xides of linoleoylethanolamide interact with ABA signaling to arrest root development during Arabidopsis seedling establishment*. Plant J, 2015. 82 (2): p. 315-27.

152. Keereetaweep, J. and K. D. Chapman, *Lipidomic Analysis of Endocannabinoid Signaling: Targeted Metabolite Identification and Quantification*. Neural Plast, 2016. 2016: p. 2426398.

153. Reisenberg, M., et al., *The diacylglycerol lipases: structure, regulation and roles in and beyond endocannabinoid signalling*. Philos Trans R Soc Lond B Biol Sci, 2012. 367 (1607): p. 3264-75.

154. Ignatowska-Jankowska, B. M., et al., *In vivo characterization of the highly selective monoacylglycerol lipase inhibitor KML29: antinociceptive activity without cannabimimetic side effects*. Br J Pharmacol, 2014. 171 (6): p. 1392-407.

155. Niphakis, M. J., et al., *Evaluation of NHS carbamates as a potent and selective class of endocannabinoid hydrolase inhibitors*. ACS Chem Neurosci, 2013. 4 (9): p. 1322-32.

156. Hsu, K. L., et al., *Discovery and optimization of piperidyl-1.2.3-triazole ureas as potent, selective, and in vivo-active inhibitors of alpha beta-hydrolase domain containing 6 (ABHD6)*. J Med Chem, 2013. 56 (21): p. 8270-9.

157. Manterola, A., et al., *Re-examining the potential of targeting ABHD6 in multiple sclerosis: Efficacy of systemic and peripherally restricted inhibitors in experimental autoimmune encephalomyelitis*. Neuropharmacology, 2018. 141: p. 181-191.

158. Millan, M. J., *Descending control of pain*. Prog Neurobiol, 2002. 66 (6): p. 355-474.

159. Sandweiss, A. J., et al., *17-beta-Estradiol induces spreading depression and pain behavior in alert female rats*. Oncotarget, 2017. 8 (69): p. 114109-114122.

160. Kiritoshi, T., G. Ji, and V. *Neugebauer, Rescue of Impaired mGluR5-Driven Endocannabinoid Signaling Restores Prefrontal Cortical Output to Inhibit Pain in Arthritic Rats*. The Journal of neuroscience: the official journal of the Society for Neuroscience, 2016. 36 (3): p. 837-850.

161. Chen, Z., et al., *Sphingosine-1-phosphate receptor 1 activation in astrocytes contributes to neuropathic pain*. Proc Natl Acad Sci USA, 2019. 116 (21): p. 10557-10562.

162. Edwards, K. A., et al., *A Kappa Opioid Receptor Agonist Blocks Bone Cancer Pain Without Altering Bone Loss. Tumor Size, or Cancer Cell Proliferation in a Mouse Model of Cancer-Induced Bone Pain*. J Pain, 2018. 19 (6): p. 612-625.

163. Ibrahim, M. M., et al., *Long-lasting antinociceptive effects of green light in acute and chronic pain in rats*. Pain, 2017. 158 (2): p. 347-360.

164. Largent-Milnes, T. M., et al., *Building a Better Analgesic: Multifunctional Compounds that Address Injury-Induced Pathology to Enhance Analgesic Efficacy while Eliminating Unwanted Side Effects*. Journal of Pharmacology and Experimental Therapeutics, 2013. 347 (1): p. 7-19.

165. Largent-Milnes, T. M., et al., *Oxycodone plus ultra-low-dose naltrexone attenuates neuropathic pain and associated mu-opioid receptor-Gs coupling*. J Pain, 2008. 9 (8): p. 700-13.

166. Marshall, T. M., et al., *Activation of descending pain-facilitatory pathways from the rostral ventromedial medulla by cholecystokinin elicits release of prostaglandin-E (2) in the spinal cord*. Pain, 2012. 153 (1): p. 86-94.

167. Thompson, A. L., T. M. Largent-Milnes, and T. W. Vanderah, *Animal Models for the Study of Bone-Derived Pain*. Methods Mol Biol, 2019. 1914: p. 391-407.

168. Vanderah, T. W., et al., *Novel D-amino acid tetrapeptides produce potent antinociception by selectively acting at peripheral kappa-opioid receptors*. Eur J Pharmacol, 2008. 583 (1): p. 62-72.

169. Zhang, H., et al., *Peripherally restricted cannabinoid 1 receptor agonist as a novel analgesic in cancer-induced bone pain*. Pain, 2018. 159 (9): p. 1814-1823.

170. Mechoulam, R., et al., *Identification of an endogenous 2-monoglyceride, present in canine gut, that binds to cannabinoid receptors*. Biochem Pharmacol, 1995. 50 (1): p. 83-90.

171. Sugiura, H., et al., *Role of peroxynitrite in airway microvascular hyperpermeability during late allergic phase in guinea pigs*. American Journal of Respiratory and Critical Care Medicine, 1999. 160 (2): p. 663-671.

172. Sugiura, T., et al., *Evidence that 2-arachidonoylglycerol but not N-palmitoylethanolamine or anandamide is the physiological ligand for the cannabinoid CB2 receptor. Comparison of the agonistic activities of various cannabinoid receptor ligands in HL-60 cells*. J Biol Chem, 2000. 275 (1): p. 605-12.

173. Diaz, P., et al., *Design and synthesis of a novel series of N-alkyl isatin acylhydrazone derivatives that act as selective cannabinoid receptor 2 agonists for the treatment of neuropathic pain*. J Med Chem, 2008. 51 (16): p. 4932-47.

174. Fang, Q., et al., *Effects of neuropeptide FF system on CB (1) and CB (2) receptors mediated antinociception in mice*. Neuropharmacology, 2012. 62 (2): p. 855-64.

175. Ledent, C., et al., *Unresponsiveness to cannabinoids and reduced addictive effects of opiates in CB1 receptor knockout mice*. Science, 1999. 283 (5400): p. 401-4.

176. Naguib, M., et al., *MDA7: a novel selective agonist for CB2 receptors that prevents allodynia in rat neuropathic pain models*. Br J Pharmacol, 2008. 155 (7): p. 1104-16.

177. Rahn, E. J., A. Makriyannis, and A. G. Hohmann, *Activation of cannabinoid CB1 and CB2 receptors suppresses neuropathic nociception evoked by the chemotherapeutic agent vincristine in rats*. Br J Pharmacol, 2007. 152 (5): p. 765-77.

178. Ryberg, E., et al., *The orphan receptor GPR55 is a novel cannabinoid receptor*. Br J Pharmacol, 2007. 152 (7): p. 1092-101.

179. Cheer, J. F., et al., *Cannabinoids enhance subsecond dopamine release in the nucleus accumbens of awake rats*. J Neurosci, 2004. 24 (18): p. 4393-400.

180. Kargl, J., et al., *A Selective Antagonist Reveals a Potential Role of G Protein-Coupled Receptor 55 in Platelet and Endothelial Cell Function*. Journal of Pharmacology and Experimental Therapeutics, 2013. 346 (1): p. 54

181. AlSuleimani, Y. M. and C. R. Hiley, *The GPR55 agonist lysophosphatidylinositol relaxes rat mesenteric resistance artery and induces Ca(2+) release in rat mesenteric artery endothelial cells*. Br J Pharmacol, 2015. 172 (12): p. 3043-57.

182. Bouchard, J., et al., *Cannabinoid receptor 2 signaling in peripheral immune cells modulates disease onset and severity in mouse models of Huntington's disease*. The Journal of neuroscience: the official journal of the Society for Neuroscience, 2012. 32 (50): p. 18259-18268.

183. Grenald, S. A., et al., *Targeting the SIP SIPRI axis mitigates cancer-induced bone pain and neuroinflammation*. Pain, 2017. 158 (9): p. 1733-1742.

184. Moutal, A., et al., *Cdk5-mediated CRMP 2 phosphorylation is necessary and sufficient for peripheral neuropathic pain*. Neurobiol Pain, 2019. 5.

185. Wilkerson, J. L., et al., *The Selective Monoacylglycerol Lipase Inhibitor MJN110 Produces Opioid-Sparing Effects in a Mouse Neuropathic Pain Model*. J Pharmacol Exp Ther, 2016. 357 (1): p. 145-56.

186. Naydenov A. V. et al., *ABHD6 blockade exerts antiepileptic denvity in PTZ-induced seizures and in spontaneous seizures in R6/2 mice*. Neuron. 2014. 83 (2): 361-371

What is claimed is:

1. A method comprising administering to a human subject suffering from a headache a pharmaceutical composition capable of enhancing arachidonoylglycerol (2AG) tone and/or inhibiting prostaglandin activity in the brain, wherein the human subject is suffering from a headache characterized with 1) decreased 2AG levels in the periaqueductal grey (PAG) brain region, and 2) unaltered anandamide (AEA) levels in the trigeminal ganglia (TG) brain region, wherein the pharmaceutical composition capable of enhancing 2AG tone and/or reducing prostaglandin activity in the mammal comprises MJN110 and KT182.

2. The method of claim 1, wherein the headache is a non-migraine headache.

3. The method of claim 1, wherein the headache is a migraine headache.

4. The method of claim 1, wherein the migraine headache is a chronic migraine headache or an episodic migraine headache.

5. The method of claim 1, further comprising co-administration of a pharmaceutical composition comprising a second agent, wherein the second agent is selected from 5-HT1 agonists, triptans, ergot alkaloids, and non-steroidal anti-inflammatory drugs.

* * * * *

SEQUENCE LISTING

```
<160> NUMBER OF SEQ ID NOS: 1

<210> SEQ ID NO 1
<211> LENGTH: 52
<212> TYPE: DNA
<213> ORGANISM: Homo sapiens

<400> SEQUENCE: 1

cggatggaca gtacctcttt tgtaggtact ggaagcccag tggcacaccc aa            52
```